US008906669B2

(12) United States Patent
Dimov et al.

(10) Patent No.: US 8,906,669 B2

(45) Date of Patent: Dec. 9, 2014

(54) MICROFLUIDIC MULTIPLEXED CELLULAR AND MOLECULAR ANALYSIS DEVICE AND METHOD

(75) Inventors: Ivan Dimov, Puerto Montt (CL); Jens Ducree, Ashbourne (IE); Luke Lee, Orinda, CA (US); Gregor Kijanka, Dublin (IE)

(73) Assignee: Dublin City University, Dublin (IE)

( * ) Notice: Subject to any disclaimer, the term of this patent is extended or adjusted under 35 U.S.C. 154(b) by 117 days.

(21) Appl. No.: 13/123,491

(22) PCT Filed: Oct. 9, 2009

(86) PCT No.: PCT/EP2009/063229

§ 371 (c)(1), (2), (4) Date: Jul. 12, 2011

(87) PCT Pub. No.: WO2010/040851

PCT Pub. Date: Apr. 15, 2010

(65) Prior Publication Data

US 2011/0262906 A1 Oct. 27, 2011

(30) Foreign Application Priority Data

Oct. 10, 2008 (GB) .................................. 0818579.5

(51) Int. Cl.

| | |
|---|---|
| ***C12M 1/00*** | (2006.01) |
| ***C12M 1/34*** | (2006.01) |
| ***C12M 3/00*** | (2006.01) |
| ***C12Q 1/68*** | (2006.01) |
| ***G01N 33/53*** | (2006.01) |
| ***B01L 3/00*** | (2006.01) |

(52) U.S. Cl.

CPC ..... *B01L 3/50273* (2013.01); *B01L 2400/0457* (2013.01); *B01L 2300/0851* (2013.01); *B01L 2200/10* (2013.01); *B01L 2200/0668* (2013.01); *B01L 2200/027* (2013.01); *B01L 2200/0647* (2013.01); *B01L 3/502761* (2013.01); *B01L 2300/0887* (2013.01); *B01L 2300/0816* (2013.01); *B01L 2400/0472* (2013.01)

USPC ....... 435/283.1; 435/6.1; 435/7.1; 435/287.2; 435/288.5; 422/68.1

(58) Field of Classification Search

USPC .................. 435/6.1, 7.1, 283.1, 287.2, 288.5; 422/68.1

See application file for complete search history.

(56) References Cited

U.S. PATENT DOCUMENTS

| | | | | |
|---|---|---|---|---|
| 6,180,415 | B1 | 1/2001 | Schultz et al. | 436/518 |
| 6,818,435 | B2 * | 11/2004 | Carvalho et al. | 435/286.5 |
| 2004/0224300 | A1 * | 11/2004 | Terashima et al. | 435/2 |

FOREIGN PATENT DOCUMENTS

| | | |
|---|---|---|
| EP | 1833693 | 2/2008 |

OTHER PUBLICATIONS

Dimov et al, Integrated microfluidic array plate (iMAP) for cellular and molecular analysis, 2011, Lab Chip, 11, 2701-2710.*

Cioffi et al., "Shear Stress and Cell Docking Inside Microfluidic Systems: A Computational and Experimental Study," Journal of Biomechanics 41(S1), 1 page, 2008.

Deutsch et al., "A Novel Miniature Cell Retainer for Correlative High-Content Analysis of Individual Untethered Non-Adherent Cells," Lab on a Chip 6:995-1000, 2006.

Figallo et al., "Micro-Bioreactor Array for Controlling Cellular Microenvironments," Lab on a Chip 7:710-719, 2007.

Horner et al., "Transport in a Grooved Perfusion Flat-Bed Bioreactor for Cell Therapy Applications," Biotechnol. Prog. 14:689-698, 1998.

Khademhosseini et al., "Molded Polyethylene Glycol Microstructures for Capturing Cells Within Microfluidic Channels," Lab on a Chip 4:425-430, 2004.

Khademhosseini et al., "Cell Docking Inside Microwells Within Reversibly Sealed Microfluidic Channels for Fabricating Multiphenotype Cell Arrays," Lab on a Chip 5:1380-1386, 2005.

Manbachi et al., "Microcirculation Within Grooved Substrates Regulates Cell Positioning and Cell Docking Inside Microfluidic Channels," Lab on a Chip 8:747-754, 2008.

Park et al., "Microfabricated Grooved Substrates as Platforms for Bioartificial Liver Reactors," Biotechnology and Bioengineering 90(5):632-644, 2005.

Park et al., "Radial Flow Hepatocyte Bioreactor Using Stacked Microfabricated Grooved Substrates," Biotechnology and Bioengineering 99(2):455-467, 2008.

International Search Report, mailed Apr. 23, 2010, for PCT/EP2009/063229, 8 pages.

International Preliminary Report on Patentability and Written Opinion, mailed Apr. 21, 2011, for PCT/EP2009/063229, 15 pages.

* cited by examiner

*Primary Examiner* — Narayan Bhat

(74) *Attorney, Agent, or Firm* — Seed IP Law Group PLLC

(57) ABSTRACT

A sequential flow analysis tool comprising a microfluidic device having a fluid path defined within a substrate between an input and an output is described. The device includes a capture chamber provided within but offset from the fluid path, the capture chamber extending into the substrate in a direction substantially perpendicular to the fluid path such that operably particles provided within a fluid flowing within the fluid path will preferentially collect within the capture chamber.

21 Claims, 21 Drawing Sheets

MICROFLUIDIC MULTIPLEXED CELLULAR AND MOLECULAR ANALYSIS DEVICE AND METHOD

FIELD OF THE INVENTION

The present invention relates to microfluidic devices and to analysis conducted using such devices. The invention more particularly relates to a microfluidic device and method that can be used for multiplexed cellular and molecular analysis and treatment.

BACKGROUND

Microfluidic devices are well known for use in analysis and sample treatment. Such devices provide for the precise control and manipulation of fluids and are generally considered to have geometric dimensions of the micro, i.e. sub-millimeter scale. These devices are particularly useful in that they provide measurements in scenarios where there are only small volumes of the analyte available or small amounts of reagents should be used, e.g. in high-throughput screening for drug discovery. Furthermore they tend to provide results with reduced reagent consumption and analysis time, ease of integration, and the potential for high-throughput analysis.

While conventional microfluidic devices provide many advantages commensurate with their dimensions there are still problems in using these devices for complete analysis systems, i.e. the type of systems that enables the provision of an analyte, the modification of that analyte and the obtaining of results from that modification. There is a further need for systems that provide a plurality of data signal outputs that can be used for statistical analysis and for parallel processing of a plurality of different tests. Also the costs of manufacturing have to be minimized, restricting the scope of fabrication technologies and hence also the degree of freedom available for the device features geometries.

SUMMARY

These and other problems are addressed by a sequential flow microfluidic device having a fluid path defined within a substrate between an input and an output, the device including a capture chamber provided within the fluid path, the capture chamber extending into the substrate in a direction substantially perpendicular to the fluid path such that operably particles provided within a fluid flowing within the fluid path will preferentially collect within the capture chamber. The chamber is desirably dimensioned to allow for the sequential flow of a plurality of fluids passed the chamber, a second fluid flow providing for a change in the medium within the chamber resultant from the first fluid flow.

The capture or collection chamber is desirably in the form of a trench having a mouth adjacent to and in fluid communication with the fluid path, the trench having sidewalls that extend downwardly into the substrate from the mouth of the trench.

In a first arrangement the particles are cells and the capture chamber is desirably dimensioned such that cells entrained within the fluid will preferentially be displaced from the fluid and will remain in the capture chamber.

The fluid path is desirably along an axis substantially parallel to the surface of the substrate. The fluid path is desirably provided proximal to an upper surface of the substrate.

In one arrangement the inlet is dimensioned to receive a pipette funnel such that fluid may be introduced downwardly into the device and then pass within the fluid path along the surface of the substrate.

The fluid path may include a funnel constriction provided between the inlet and the capture chamber so as to effect a filtering of particulate matter of a predetermined dimension prior to the capture chamber.

The device may be configured in an array structure with a plurality of capture chambers. Desirably the plurality of capture chambers share a common input and output, the input being arranged in a branch structure such that fluid introduced into the input will be directed towards each of the capture chambers.

There is also provided a multiplexed structure including a plurality of devices arranged on a common substrate.

The invention also provides a methodology for effecting cell or molecular analysis.

Accordingly, a first embodiment of the invention provides an apparatus as detailed in claim 1. A tool according to claim 13 is also provided. Advantageous embodiments are provided in the dependent claims.

These and other features will be better understood with reference to the exemplary arrangements which follow.

BRIEF DESCRIPTION OF THE DRAWINGS

The present invention will now be described with reference to the accompanying drawings in which.

DETAILED DESCRIPTION OF THE DRAWINGS

The teaching of the invention will now be described with reference to exemplary arrangements thereof which are provided to assist in an understanding of the teaching of the invention but which are not in any way intended to limit the scope of the invention to that described.

Figure 1:
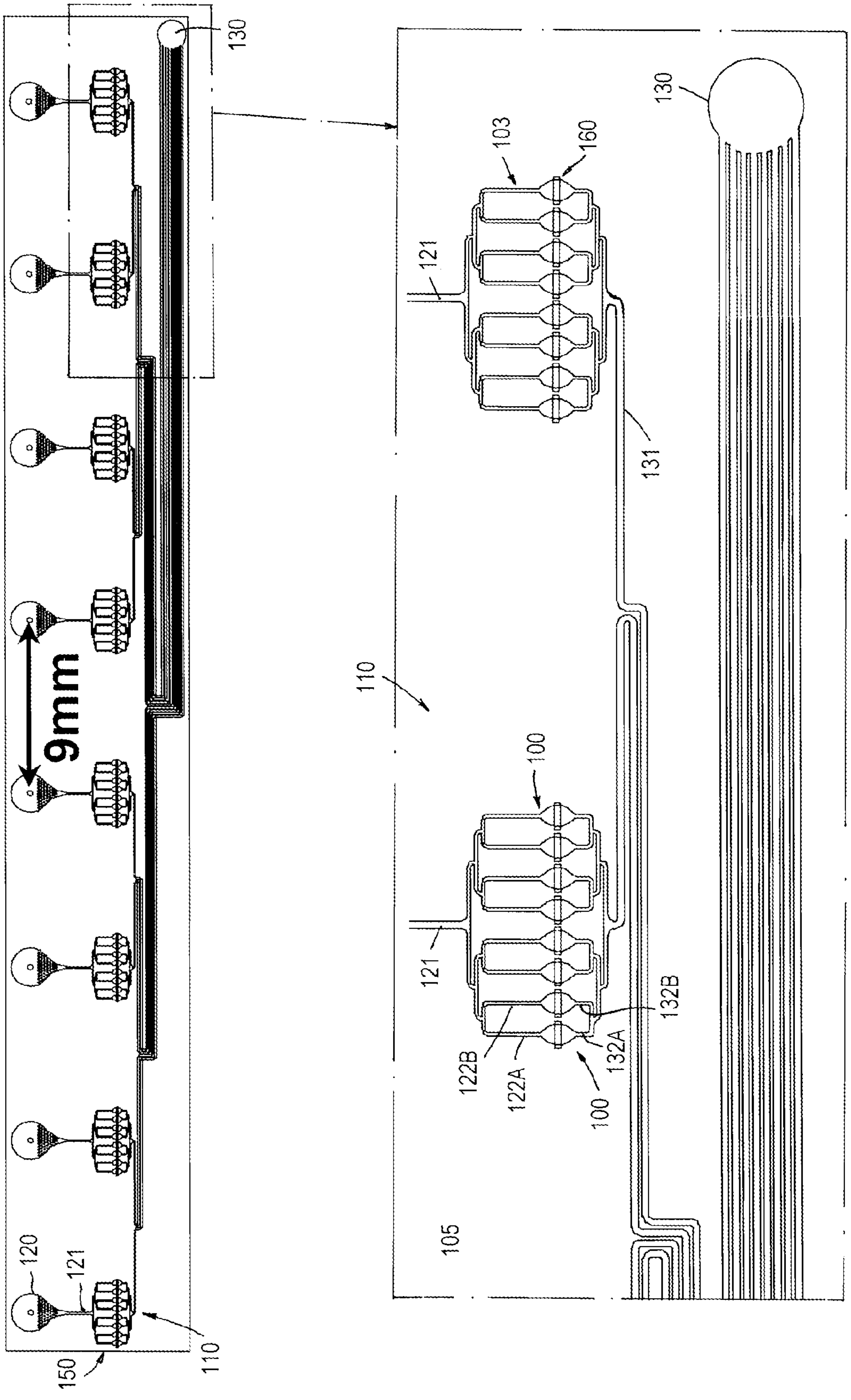
FIG. 1 shows an array of devices provided in a row configuration in accordance with the present teaching
Figure 2:
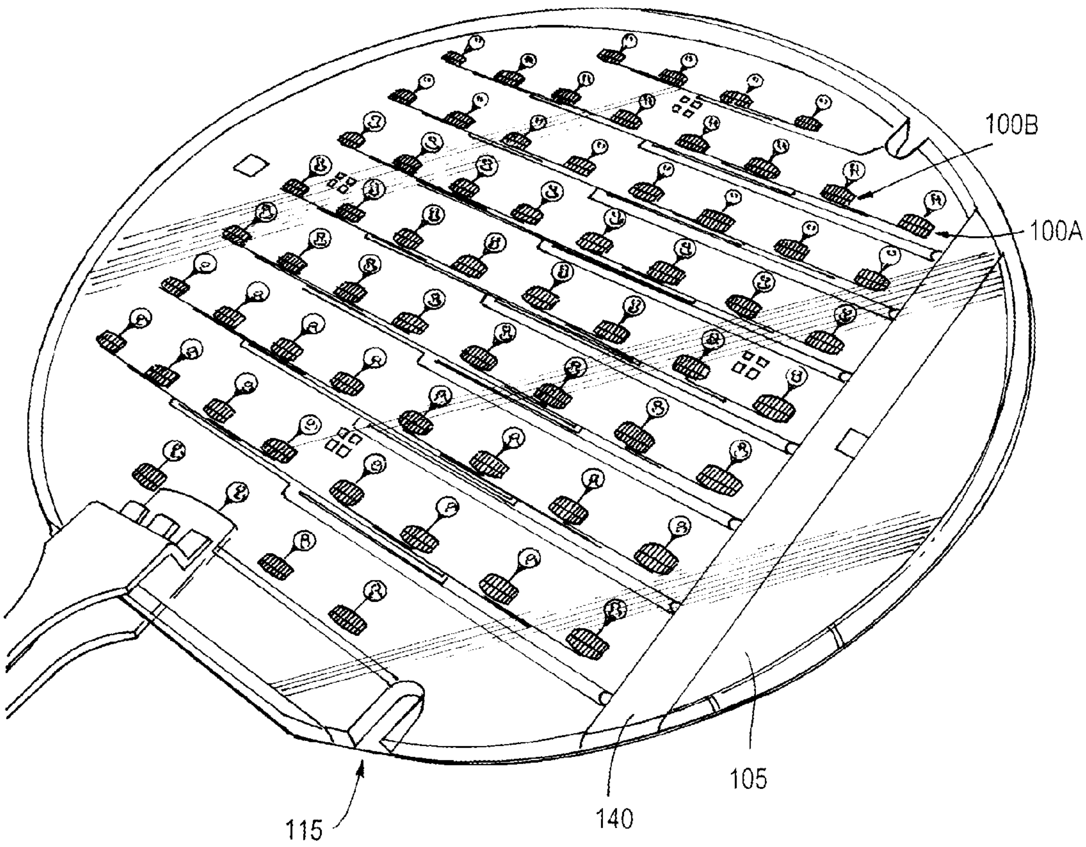
FIG. 2 is a photograph of an exemplary multiplexed structure including a plurality of devices.

FIGS. 1 and 2 show an exemplary structure incorporating a microfluidic device 100 in accordance with the present teaching. Each device 100 comprises a fluid path 103 defined within a substrate 105 between an input 120 and an output 130. A capture chamber 160 is provided within the fluid path. The capture chamber is configured so as to extend into the substrate in a direction substantially perpendicular to the fluid path such that operably particles provided within a fluid flowing within the fluid path will preferentially collect within the capture chamber by means of a substantially perpendicular force field enforcing sedimentation. In this exemplary arrangement the capture chamber extends downwardly into the substrate. In this way it can be considered as having a major axis which is substantially perpendicular to the plane of the substrate surface.

Typically the device will be operated in a horizontal arrangement such that the direction of extension of the chamber is parallel with gravitational force lines, i.e. the particles within the fluid will be biased towards the bottom of the chamber under the influence of gravity. It will be understood that gravity is an example of a non-centrifugal force in that it acts on the particles without requiring a movement of the device, and within the context of the present teaching any force that does not rely on rotation of the device to effect retention of the particles within the chamber can be considered suitable. In contrast to the forces causing retention of the particles within the chamber, centrifugal forces could be considered suitable for effecting movement of the fluid within the fluid flow. It will be appreciated that the forces that effect displacement of the particles from the fluid and their subsequent retention in the chamber act substantially perpendicular to the direction of flow of the fluid.

The device is particularly suitable for configuring in array structures, a plurality of arrays being integrated into a multiplexed structure. Each of the devices 100 of FIGS. 1 and 2 may be considered identical and are usefully employed as Cell Capture and Processing Elements (CCPE) such that the completely integrated and multiplexed device shown in FIGS. 1 and 2 provides five hundred and twelve identical Cell Capture and Processing Elements (CCPE) multiplexed into a single monolithic device. It will be appreciated that the specific number is related to the exemplary arrangement of nine non-identical rows of arrays, the total structure having sixty four arrays each having eight microfluidic devices, but different configurations could be provided without departing from the teaching of the present invention.

Each array 110 in this configuration comprises eight identical devices 100, sharing a common input 120 and a common output 130. The common input branches into 8 feed lines 122*a*, 122*b*, 122*c* etc., provided upstream of capture chambers for each device respectively. Each device has a dedicated waste line 132*a*, 132*b*, 132*c* etc., provided downstream of the capture chamber and configured to distribute fluid out of the devices into the common output 130. Within each array it will therefore be understood that a plurality of capture chambers are provided. Where they share a common input the fluids that are discharged into the individual chambers will be the same. However by pre-treating individual chambers it may be possible to vary the conditions experienced by those fluids within the individual chambers.

Individual arrays 110 may be arranged in rows 150*a*, 150*b* etc., on the substrate 105. In this way a plurality of arrays may be aligned; in this exemplary arrangement along a common row. Where a plurality of arrays are provided along a common axis, they may advantageously be configured so as to share a common waste. In this exemplary arrangement the common output 130 for each row is then in fluid communication with common waste 140 for the multiplexed structure.

In this exemplary arrangement, each inlet is evenly connected to 8 CCPEs 100 and the inlets 120 have the same distribution as a 96 conventional well micro titter plate—approximately 9 mm apart from one another as shown in FIG. 1. The devices of this arrangement are configured to be loaded with fluid under the influence of a hydrostatic pressure head. Such loading of the fluid into the devices and then the subsequent propulsion of the fluid within the devices can be provided by coupling the devices to a pipette arrangement whereby the volume of fluid in the pipette generates a pressure that causes the fluid to enter downwardly into device from the pipette and then travel within the fluid path. In this way the multiplexed microfluidic structure 115 may be used with conventional loading equipment such that for example sample loading may be done with a standard 8 channel pipette such as those manufactured and provided by the company Eppendorf.

Figure 3:
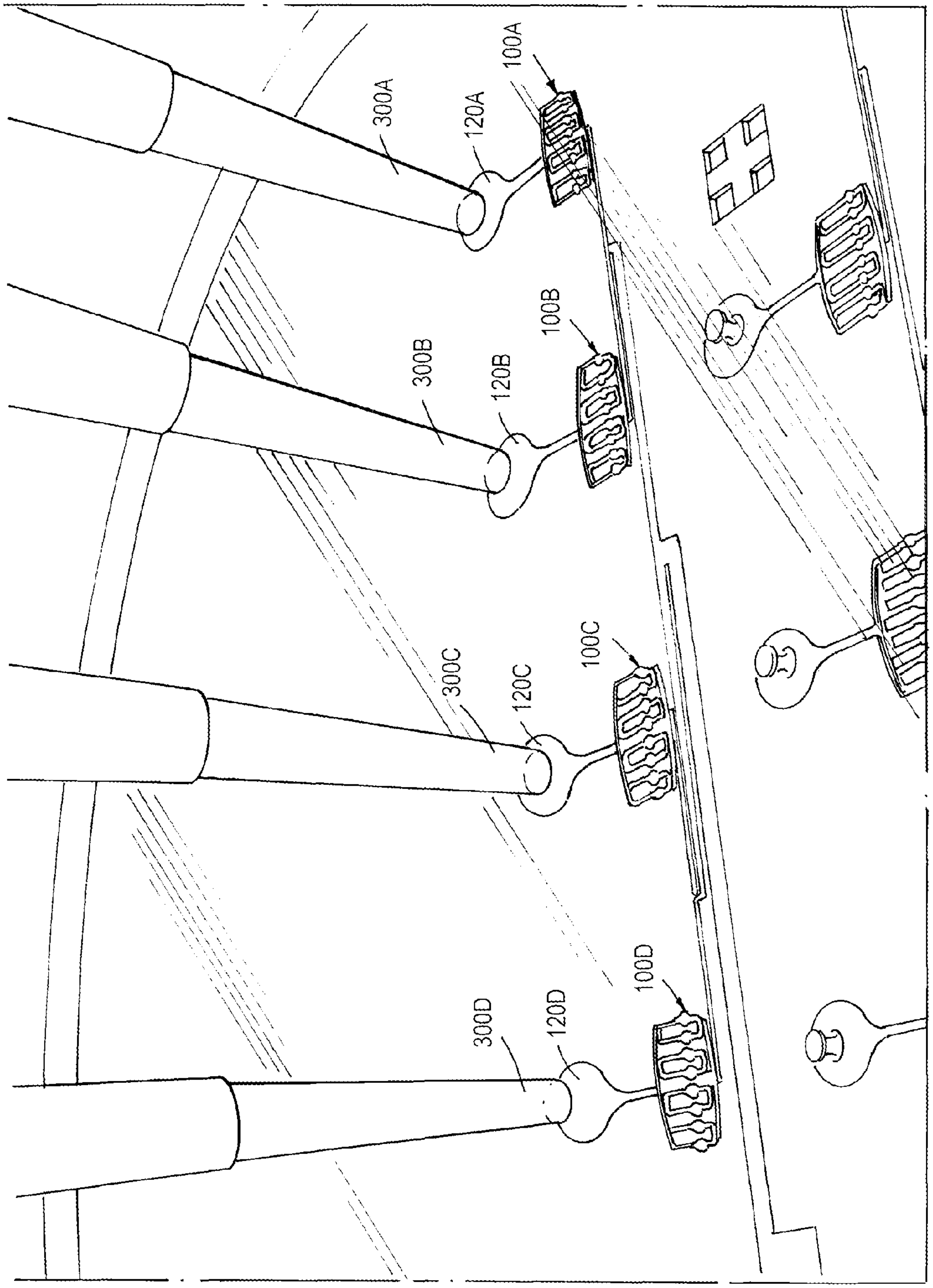
FIG. 3 is a photograph showing the loading of a structure of FIG. 2.

An example of such a loading configuration is shown in FIG. 3, where 4 conventional pipettes 300 are mated with 4 inlets respectively. Fluid within each of the 4 pipettes can be transferred into 8 individual microfluidic devices 100 arranged in an array structure, each of the devices sharing the common input 120. In the arrangement of FIG. 3, it will be observed that the loading of the multiplexed structure can be achieved on a per row basis such that each of the rows does not have to be concurrently loaded. In this way the number of experiments that is conducted can be defined relative to either the nature of experiment or the volume of analyte available. It will be appreciated that by providing a plurality of different devices coupled to the same input that each of the device serves to replicate the process being conducted in the other devices of the array. This allows statistical analysis of the process to be conducted with the comfort that the conditions of each device in the array should be identical. Two or more separate arrays can be loaded concurrently with the same or different materials—be that particles within a fluid or particles directly—such that each array either replicates the process of the other or is operable to conduct a different process concurrently with that of the other.

While pipette loading is an example of a hydrostatic pressure head delivery system other configurations such as a tilting of the device to allow for flow of the pure fluid or particle suspension within the device also could be utilised to take advantage of the principles of hydrostatic pressure. Other arrangements for fluid delivery or fluid propulsion could combine or alternate these techniques with others such as those means providing a pressure driven or a centrifugally driven or propelled flow. Another example which could be employed would be a process taking advantage of the electrokinetic phenomena. Generally speaking, any of the various flow-generating mechanisms such as those described in D J Laser and J G Santiago, J. Micromech. Microeng. 14 (2004) R35-R64 may in principle be used to generate the flow in the here described device.

The devices of the present invention are particularly well suited for providing analysis and/or treatment of very small volumes of available analyte. For example in the arrangement of FIG. 4, which is a schematic of a single device 100, typical capture volumes are about 10 nL. A device in accordance with the present teaching provides a capture chamber 160 provided in a fluid path 400 between the fluid input 120 and the output 130, the fluid path providing a conduit for fluid flowing in a direction 405 between the input and the output. In an array structure, the capture chamber is desirably located between the feed line 122 and the waste line 132. The capture chamber 160 is provided to selectively capture particles travelling within the fluid such that these particles will be displaced out of the fluid and remain in the capture chamber while the fluid exits the device.

Figure 4B:
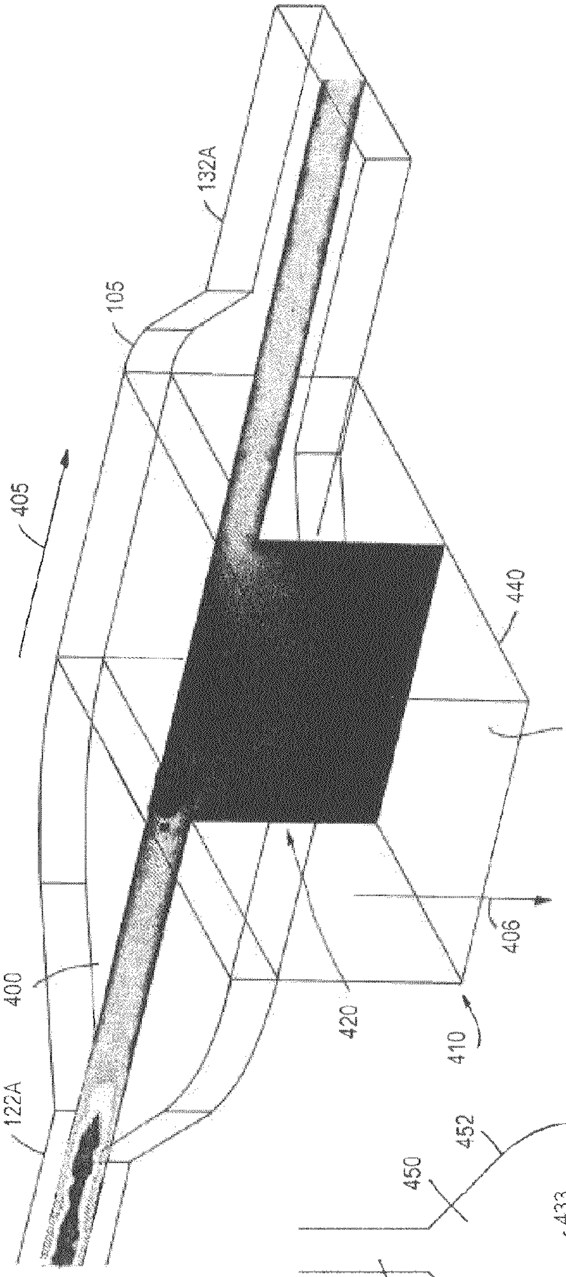
FIG. 4B shows in perspective sectional view elements of such a device.

As shown in FIG. 4B, the capture chamber is desirably a 3-D structure having a depth that extends substantially perpendicular to the fluid path. This geometry may be provided in the form of a trench 410 having a mouth 420 provided adjacent to and in fluid communication with the fluid path 400. The trench 410 has sidewalls 430 that extend downwardly into the substrate 105 from the mouth 420 of the trench. As is evident from an inspection of FIG. 4, the fluid path is desirably along an axis substantially parallel to the surface of the substrate and is desirably provided proximal to an upper surface of the substrate. While it is not intended to limit the teaching of the present invention to any one specific arrangement or geometry, the device is made of two layers, one is for the channels having dimensions of approx. 40 microns high. The trench, in contrast has a depth that extends downwardly from the surface of the substrate such that while the mouth 420 is proximal to the surface of the substrate, a base 440 of the trench is distally located to the surface of the substrate and also to the fluid path 400. This depth provided by a second layer within the device, this having a depth of approximately 300 microns.

In this exemplary arrangement the surface walls of the trench are untreated and are empty prior to the initial loading of fluid into the device. However it will be appreciated that surface coatings could be provided onto the walls of the trench for specific experiments or analysis, these coatings typically exhibiting a predefined disposition for particles of interest within the analysis to be conducted. In another modification the trench could be pre-provided with reagents such that analysis conducted using devices of the present teaching could effectively introduce particles into a reagent loaded trench.

Figure 4A:
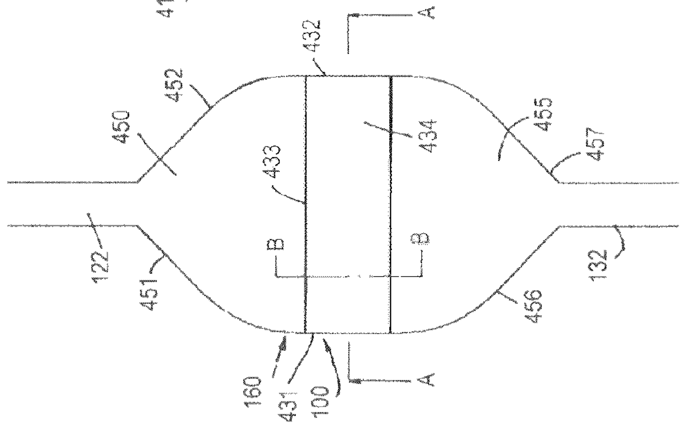
FIG. 4A shows in plan view a device provided in accordance with the present teaching.

In this exemplary configuration, and as is evident from the plan view of FIG. 4A, the trench is substantially rectangular in form having two pairs of side walls, each pair differing from the other pair in length. Desirably the trench is arranged such that its major axis (A-A') is substantially perpendicular to the direction of fluid flow 405. The minor axis (B-B') is provided parallel with the fluid flow 405. In this way the distance between a first pair of side walls 431, 432 is greater than the distance between a second pair of side walls 433, 434. The height of each pair of side walls—i.e. the overall depth of the trench is in this arrangement the same. Particles that are displaced within the chamber are biased towards the base 440 of the chamber under the influence of a force having a force vector acting in the direction of the arrow 406 which will be understood as being substantially perpendicular to the direction of fluid flow 405.

So as to allow fluid within the fluid feed line 122 to pass over the entire mouth of the trench 410, the fluid path desirably tapers outwardly in the region immediately preceding the mouth of the trench. In the fluid feed line region 122, the side walls defining the fluid path are substantially parallel. In this first taper region 450 side walls 451 452 flare away from one another such that the distance between the side walls increases as the fluid approaches the mouth 420 of the trench. This increase in cross-sectional area of the fluid path causes fluid within the fluid path to decelerate as it approaches the mouth of the trench. The length of the taper region, i.e. the distance from the fluid feed line region 122 to the mouth of the trench is desirably sufficient to allow the particles to sediment to the bottom of the trench. It will be appreciated that this is related to the speed at which the fluid is passing over the mouth of the trench and this defines an aspect ratio between the dimensions of the trench and the fluid flow rate. This can be used to design specific trenches for preferential use with specific flow rate conditions.

In a similar fashion on the far side of the trench, i.e. the region closer to the fluid waste line 132, a funnel region 455 is provided. Side walls 456, 457 of this funnel region 455 taper inwardly towards one another as the distance from the mouth of the trench increases until they form the waste line 132 where the side walls are once again parallel with one another. This funnelling is provided to redirect the fluid that was at the edge portions of the trench, i.e. adjacent to the side walls 431, 432, into a more constricted volume. This constriction results in an acceleration of the fluid as it approaches the waste line 132.

As the fluid passes over the mouth of the trench it enters downwardly into the trench. This movement out of its plane of travel causes a deceleration of the fluid. As it then exits the trench there is a corresponding increase in the velocity of the fluid. The change of velocity within the trench region causes particles within the fluid to be displaced from the fluid. Once displaced, they settle towards the base 440 of the trench under action of an external force. It will be appreciated that the trench is desirably dimensioned relative to the flow rate of the operating conditions such that once displaced the particles will be retained within the trench. It should also be noted that apart from the previously described geometrical expansion of the flow channel, the flow rate can also be adjusted in a flow channel of constant cross-section by adjusting its hydrodynamic resistance, e.g. by varying the length, cross-section of the channel or the viscosity of the fluid, and/or the pumping force, e.g. by adjusting the height of the water column of the frequency of rotation in a centrifugally pumped system.

Figure 5:
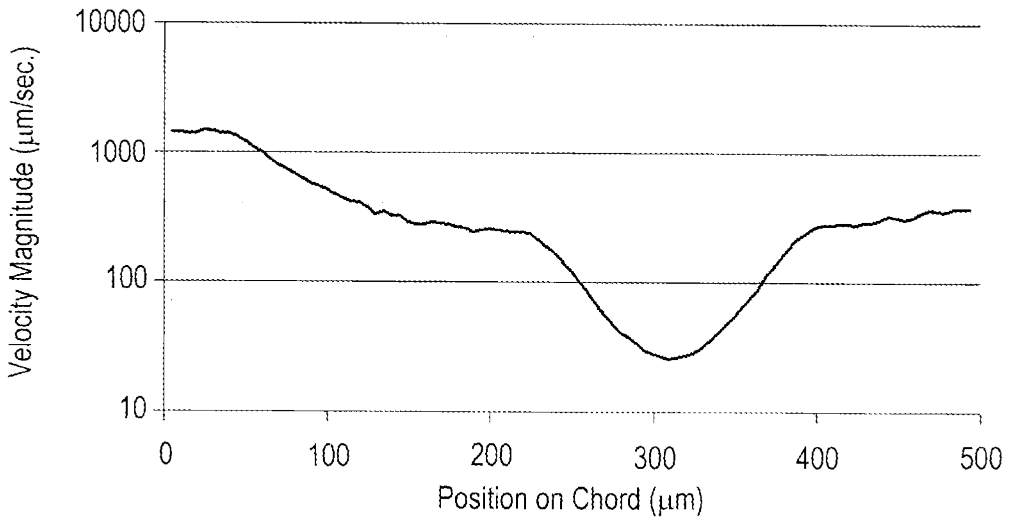
FIG. 5 shows how fluid velocity varies within the fluid path.

Simulation results of a fluid velocity within the taper region 450, the trench 410 and the funnel region 455 show these changes in velocity. As is evident from FIG. 5, the velocity of fluid within the fluid path decreases as it passes over the trench region—coincident with the region between 200 and 400 microns. It then increases again as it enters the funnel region, the area within the graph greater than 400 microns on the X axis. As it is also evident from an inspection of exemplary lengths, it is desirable that the taper region is of greater length than the funnel region.

Figure 6:
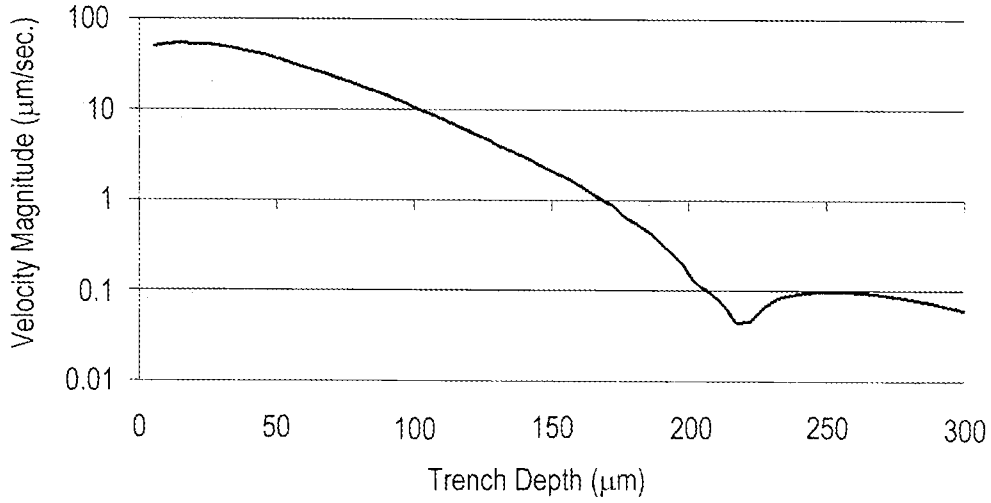
FIG. 6 shows how fluid velocity varies with depth of the collection trench.

FIG. 6 shows how fluid entering downwardly into the trench will also decelerate. As a result of this, it will be appreciated that the throughput of fluid in upper regions of the trench is greater than throughput in lower regions. This has significance in mixing of fluid samples, as will be discussed later.

A device provided in accordance with the present teaching is especially useful within the context of cell capture and in sequential flow analysis where a plurality of fluids may be passed through the same device in a sequential fashion. In such an arrangement the particles described heretofore can be considered cells and the capture chamber is desirably dimensioned such that cells entrained within the fluid will preferentially be displaced from the fluid and will remain in the capture chamber.

Figure 7:
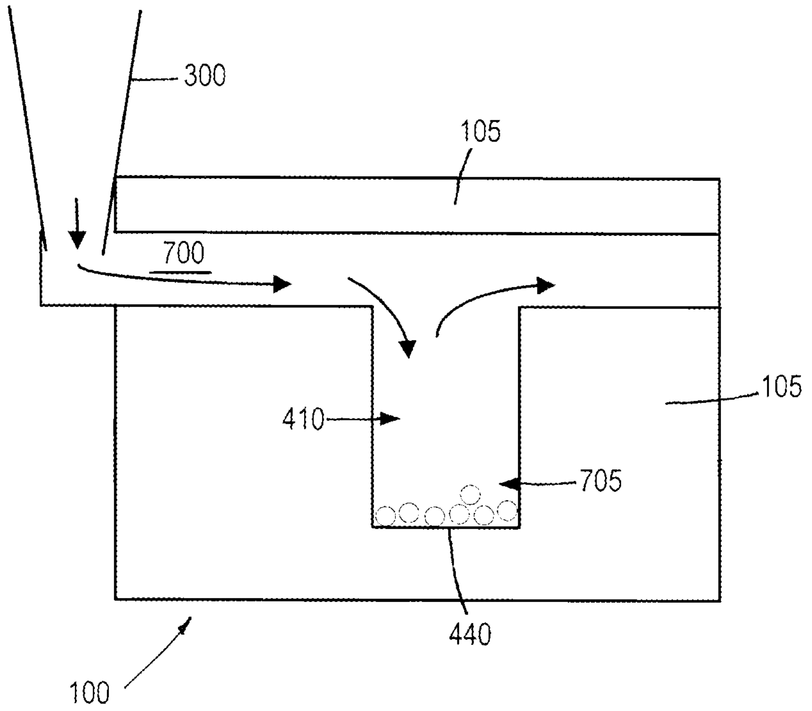
FIG. 7 shows schematically how a fluid may be introduced so as to effect capture of cells within the capture region.

FIG. 7 shows an exemplary arrangement of how cells can be effectively captured using a device 100 such as that described heretofore. A fluid 700 having a culture medium with cells of interest entrained therein is provided in a sample pipette 300. Volumes of the order of 1 to 400 microliters may be provided in the pipette. By providing an open configuration the fluid will be gravity fed in that it will enter downwardly into the device under the effect of gravity. On introduction its direction of flow is substantially parallel to the surface of the substrate prior to encountering the capture chamber or trench. In this region the fluid will pass downwardly and slow down—per FIG. 6. Any cell matter 705 within the fluid will displace from the fluid and settle on the bottom 440 of the trench under the impact of a sedimentation force with a substantial component in the direction of the capture chamber. This cell matter can be tested in any one of a number of different arrangements.

While the device heretofore described has application in any analysis technique that requires capture of cellular or other particulate matter, in that it provides for an effective capture of the cellular matter from a fluid medium in which it is conveyed, it will be further appreciated that such a capture region provides an effective experimental region wherein a capture cell can be stimulated or modified by suitable experimental techniques. By changing the fluid that is introduced in the device, captured cells can be exposed to different environments and their responses can be tested or for example their contents may be released to the surrounding solution in the capture chamber by exposure to a suitable lysis agent.

An example of such a multi-step analysis that may be effected using a device in accordance with the present teaching is NASBA analysis which it will be appreciated is a specific example of nucleic acid amplification.

Nucleic Acid Sequence-Based Amplification (NASBA) is a transcription-based RNA amplification system. Initially developed by Compton in 1991, NASBA is an isothermal (41° C.) process that can produce more than 109 copy cycles in 90 min. Compared to other in-vitro amplification methods such polymerase chain reaction (PCR), strand-displacement amplification (SDA) or rolling-circle amplification (RCA), NASBA has the unique characteristic that it can, in a single step, amplify RNA sequences. To achieve this NASBA involves the simultaneous action of three enzymes (avian myeloblastosis virus reverse transcriptase, RNase H, and T7 RNA polymerase). Several nucleic acid types, including mRNA, rRNA, tmRNA, and ssDNA, as well as nucleic acids from virus particles, can be analysed with NASBA, enabling a range of diagnostics, along with gene expression and cell viability measurements. In some cases the one step NASBA protocol can achieve levels of detection of extracted RNA a hundred times lower compared to the three step RT-PCR protocol. Furthermore, NASBA has the unique ability to specifically amplify RNA in a background of DNA of a comparable sequence, this reduces the sample purification requirements. A device such as that provided in accordance with the present teaching has specific application in NASBA analysis or indeed in other techniques that require the sequential delivery of multiple fluids.

Figure 8:
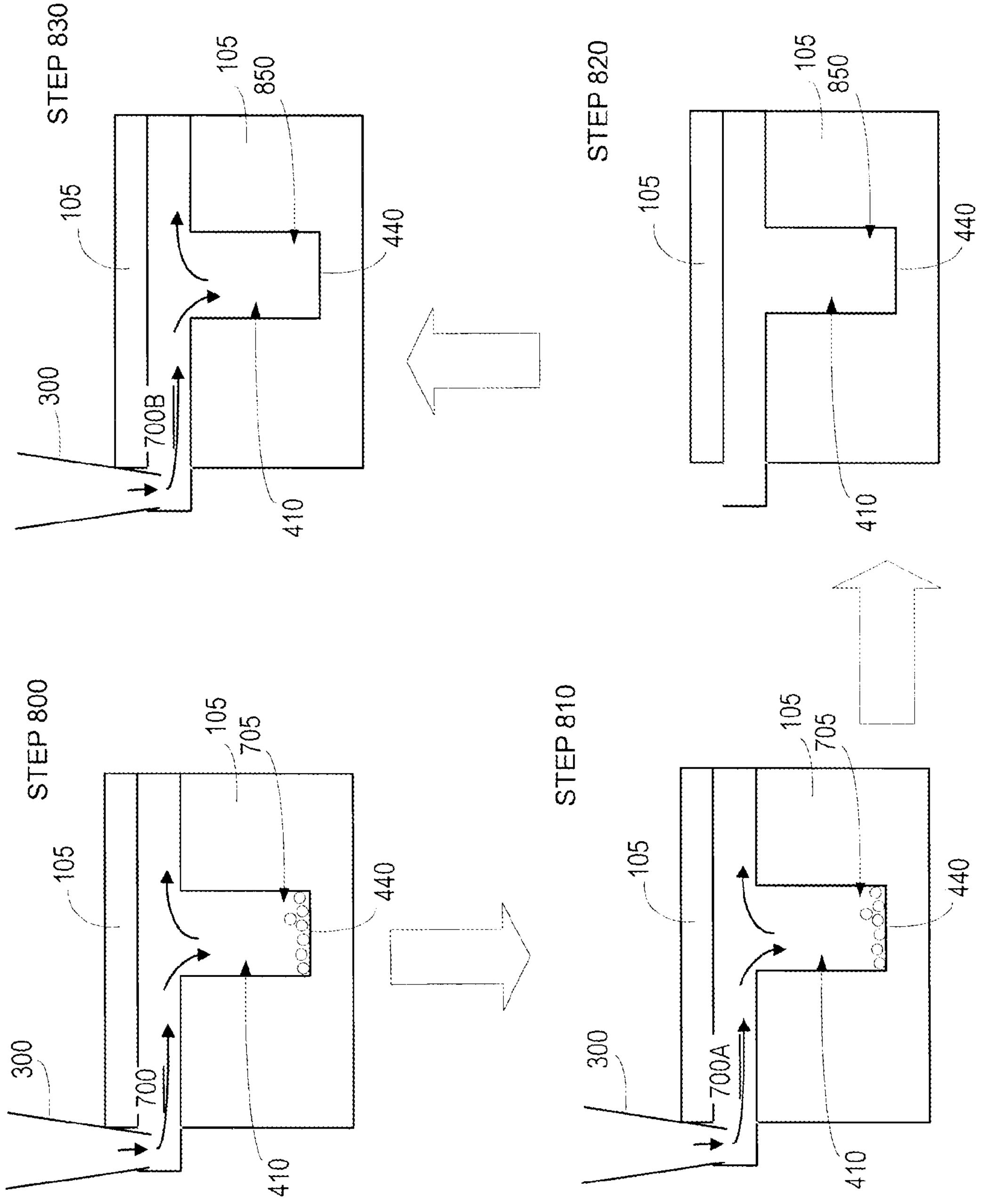
FIG. 8 shows a sequence of steps that may be implemented in a multi-flow through arrangement.

Each microfluidic device 100 or COPE element module can be configured to capture cells from a fluid passing within the device flow, long term culture them, stimulate them with drugs and agonists, stain them, lyse them and finally perform real-time NASBA analysis and/or an immuno assay analysis all within the same chamber. An example of such a methodology will be described with reference to FIG. 8.

In a first step, Step 800, a culture medium 700 is introduced into the device. This may be done in one or more repeated steps and during this cell culture phase the entire device is placed in a standard cell culture incubator where, if required, conditions such as concentration of $CO_2$ can be controlled. The presence of the culture medium and the controlled ambient conditions allow for a culturing of the cells captured within the trench. Once these have been cultured, it is then possible to change the fluid within the device.

As an example, in Step 810, a lysis mixture 700A is introduced into the device. The lysis mixture once introduced can be left in-situ within the device (Step 820) for a sufficient period of time to allow for cell lysis.

Once this period has expired, the flow through fluid can be changed again such that for example NASBA reagents 700B may be introduced into the device (Step 830). Analysis of the reaction of the lysate mixture 850 to the introduced NASBA reagents can be assessed in real time. During the real-time NASBA and immuno-assay analysis phase the device may be mounted on a standard automated temperature controlled fluorescence microscope stage and the change in fluorescence from each trench may be measured as a function of time. To simplify the operation the device is designed in such a way that the fluidic resistivity of all the inlets is equal and low enough so that the pressure generated by a standard pipette is sufficient to drive fluids into the device. This enables all fluid loading of the device to be done directly with a standard pipette and furthermore when the filled pipette tips are left plugged into the inlets they function as gravity driven pumps or hydrostatic delivery devices. This gravity driven pumping action is used for cell loading and the perfusion of culture media, drugs and labelling dyes, lysis mixture, immuno-assay and real time NASBA reagents. By varying the height of the fluid in the inlet tip the gravity driven pumping flow velocity can be controlled.

Figure 9:
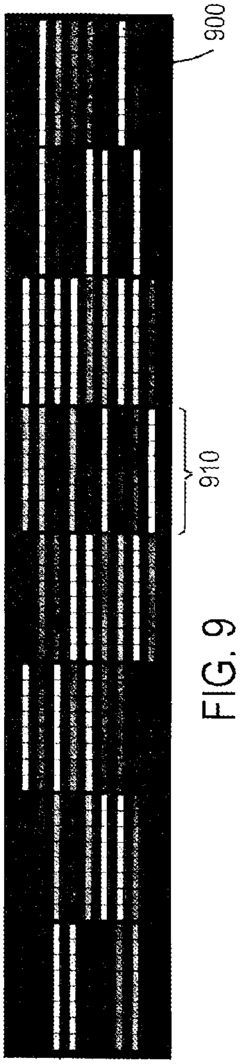
FIG. 9 shows exemplary results that may be concurrently obtained using a structure in accordance with the present teaching.

FIG. 9 shows exemplary results achieved from a multiplexed array structure such as that shown in FIG. 2. In this exemplary arrangement the signal responses 900 for each of the individual devices are evident. For example in the array 910, eight individual responses are evident. Each response is reflective of the reaction that has occurred within an individual capture chamber. It will be appreciated that by integrating a plurality of individual devices 100 onto a single substrate and effecting simultaneous experiments within each, that it is possible to obtain a plurality of results within the same time frame. Furthermore as each experiment, i.e. the results from cells captured within the individual chambers, has been conducted within the same ambient conditions, statistical errors are reduced.

Experimental Results

Figure 10:
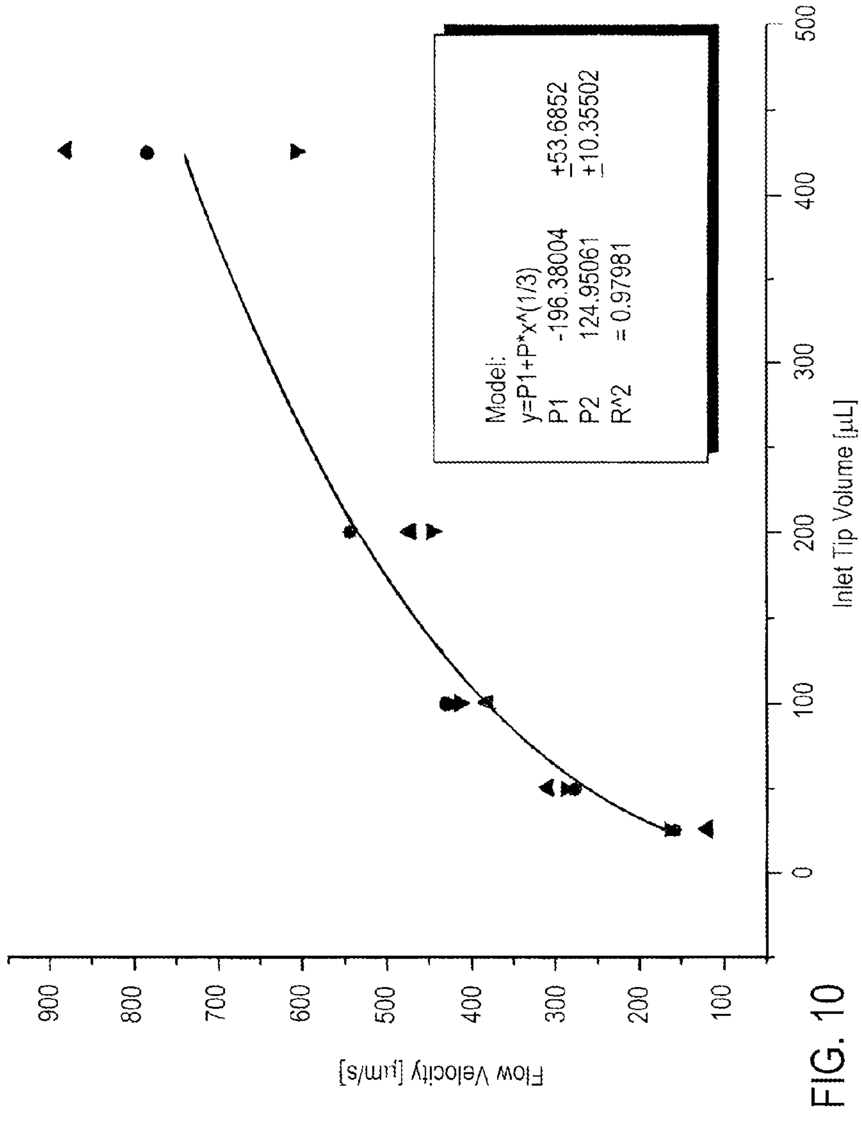
FIG. 10 shows how the volume of fluid within the inlet tip may be used to control flow rates within a device.

It will be appreciated from the foregoing that the device described utilises gravitational driven flow and the fact that fluids are responsive to hydrostatic pressure to effect a flowing of the fluid from regions of higher pressure to regions of lower pressure. To understand the effect of the device's capability of harnessing gravity driven flow inlet pipettes were filled with different volumes and measuring the flow velocity generated at the inlet of each device 100 was measured. The results are shown in FIG. 10. It is evident that by increasing the volume of fluid provided initially in each pipette that the flow rate within the device can be controlled. In this way for example, if it is desired to have a low flow rate, a smaller volume of fluid may be provided in the pipette.

The injection flow rate has an effect on cell and particulate matter loading within the trench or capture region. Cells or particles suspended in a fluid are flown into the device, and as long as the injection flow rate is below a certain threshold all cells that pass over the cavity region will sediment and be trapped within the cavity.

Figure 11:
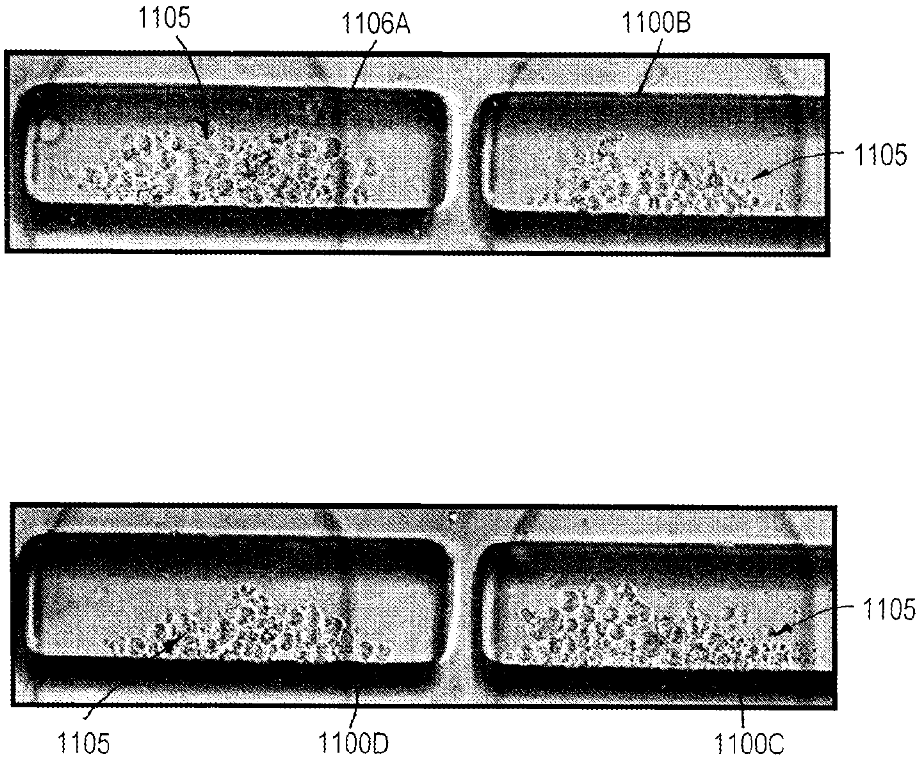
FIG. 11 shows example of cell loading.
Figure 12:
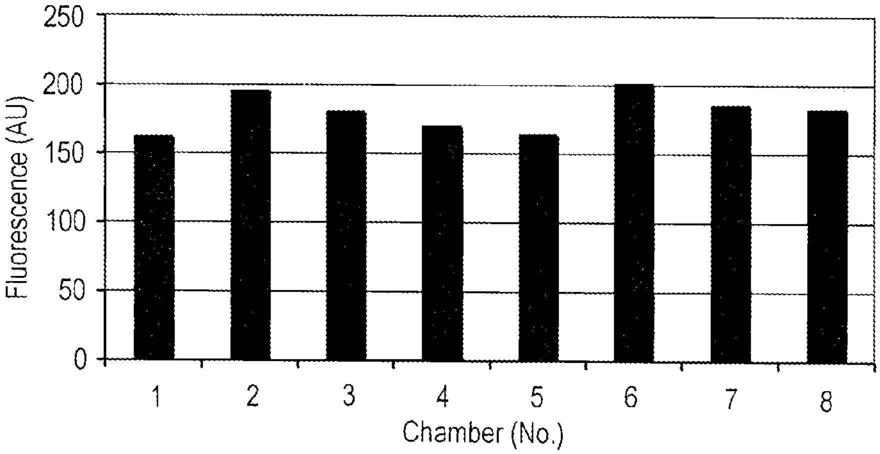
FIG. 12 shows exemplary statistical data demonstrating cell loading in different cells.

FIG. 11 illustrates a scenario where HeLa cells 1105 are trapped within several trenches 1100A, 11008, 1100C, 1100D. Each of the four trenches has identical dimensions 100×400 μm with a depth of 320 μm, while the flow path had a height of 40 μm. The injection flow rate was 50 mL/min. As is seen from a visual inspection of each of the four chambers 1100A, 11008, 1100C, 1100D, the HeLA 1105 cells are trapped within the chambers. Further statistical analysis on additional chambers as shown in FIG. 12 shows cell loading relative standard deviation of 7.8%.

Figure 13:
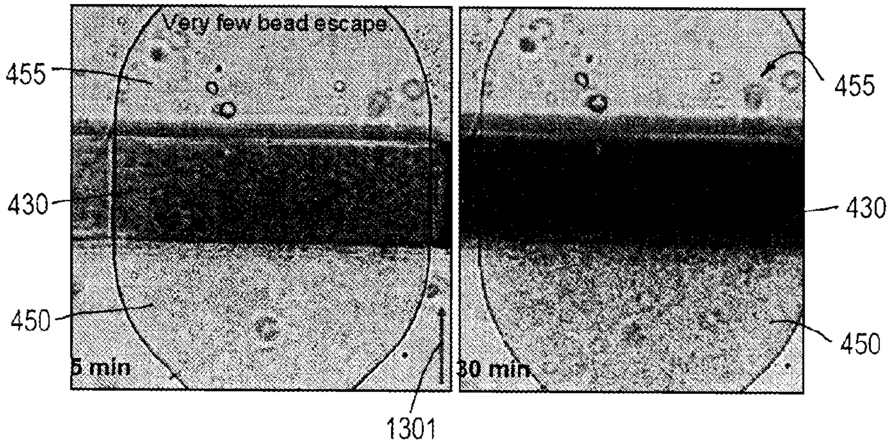
FIG. 13 shows how efficient capture is effected using an example of beads within a fluid flow.

FIG. 13 shows a modification where 1.5 μm silica beads were captured within the cavity; the reference numerals used are the same as what was used for FIG. 4. After 30 min of loading the beads have begun to fill the cavity and almost no beads were detected escaping the cavity. The same experimental conditions were employed for the arrangement of FIG. 11 as for FIG. 13. The injection flow rate was 50 mL/min in the direction of the arrow 1301. Statistical measurements have shown 99.75% capture efficiency.

Figure 14:
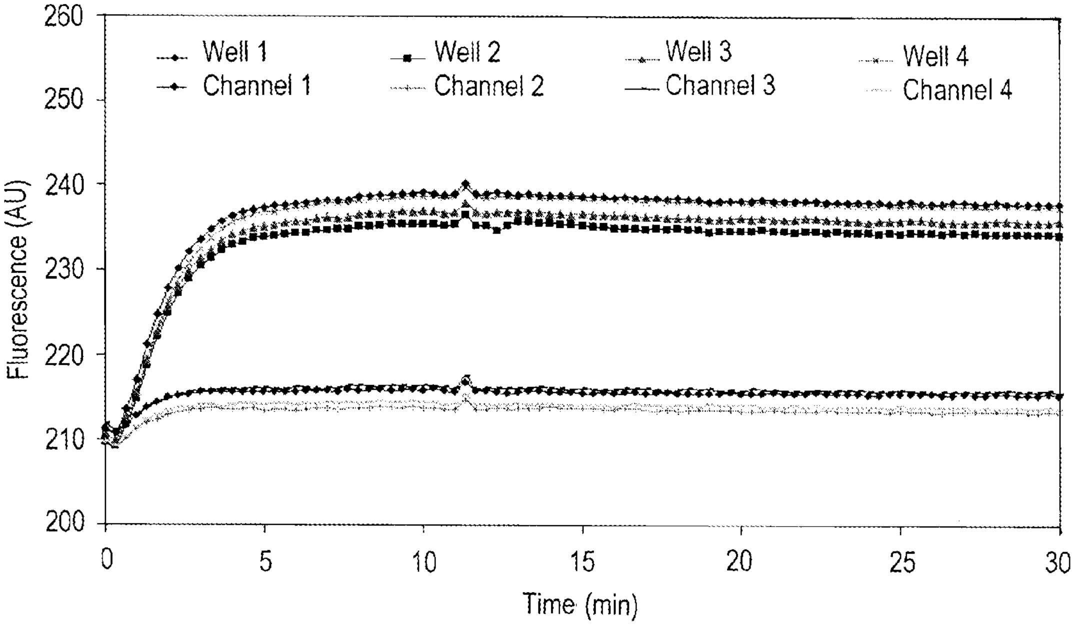
FIG. 14 shows how fluids within the trench may be replaced by flowing new fluids passed.

Using devices such as that provided within the context of the present disclosure, the fluid volume within the trench can be easily replaced with a new solution by just flowing the new solution over the cavity. This is demonstrated in the context of FIG. 14 where a fluorescent dye solution was introduced into a device having previously received water, the water being retained within a 300 micron deep trench. The flow rate was approx. 500 μm/s. Within 5 min the dye solution had completely replaced the pure water.

Figure 15:
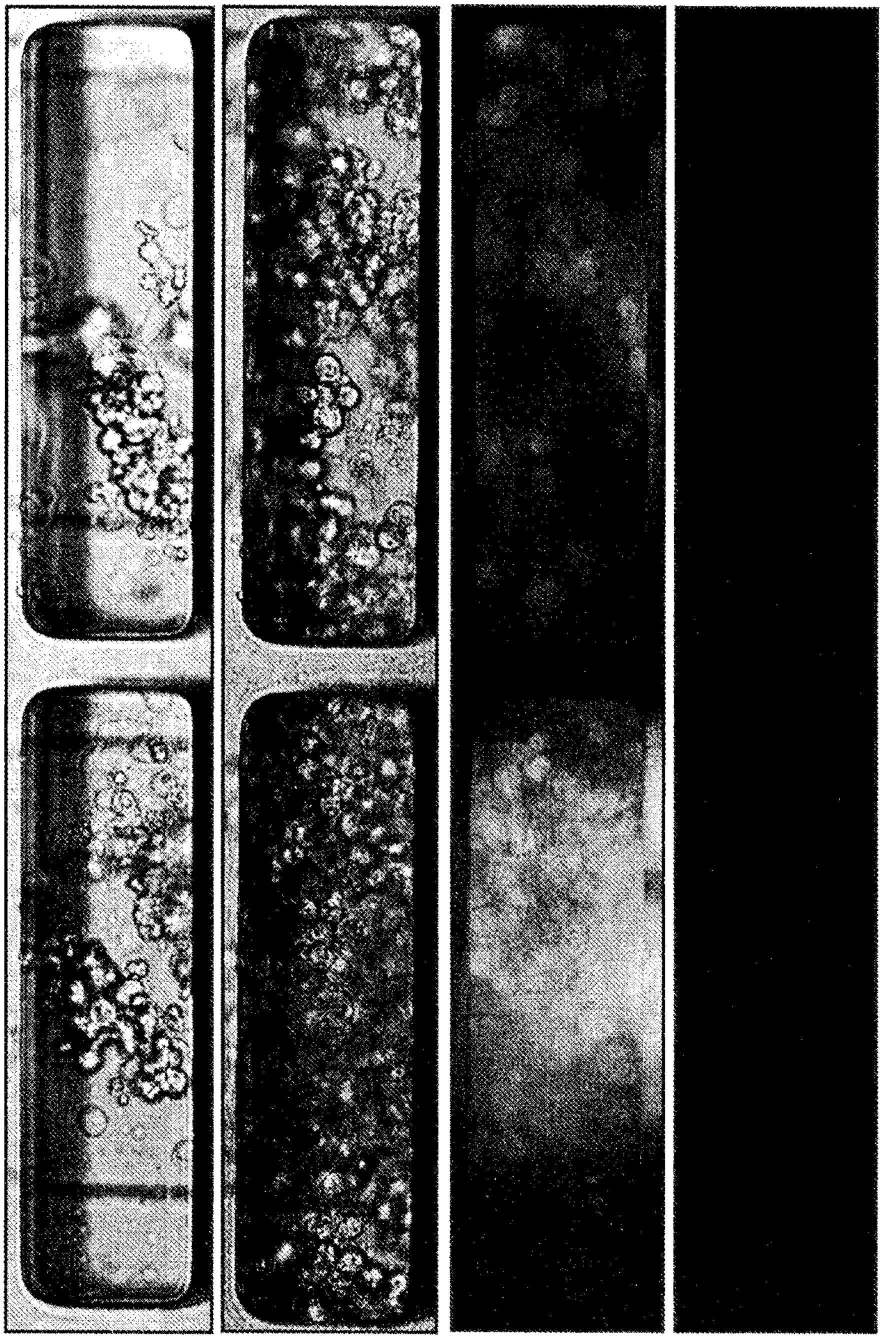
FIG. 15 shows exemplary data demonstrating how devices may be usefully employed in long term cell culturing.

To demonstrate the usefulness of a device or structure such as that heretofore described cell culture, drug stimulation and staining procedures were performed. After loading the cells into the capture regions, the device was placed within an incubation chamber at 37 C and culture media dynamically perfused over the cells through the gravity driven flow. The inlet tips were generally reloaded with new media every 2 days. The waste fluids were also cleaned off every 48 hrs. When the cells had to be stained then the media in the inlet tips was replaced with the dye solutions. After approx. 20 min of gravity driven flow of the dye solutions the cells are labelled and can be fluorescently interrogated with a microscope. Results from such steps are provided in FIG. 15 where long term cell culture and viability staining results are evident.

To demonstrate lysis and purification a layer of beads were provided on top of the cells. The beads were provided with pre-coated antibodies or oligo-nucleotide sequences that would specifically bind to the target of interest that will be purified. The cells are lysed by diffusion mixing a lysis agent and washing off the rest of the lysate. The steps are shown in FIG. 16, which again uses the same reference numerals as have been previously used for FIGS. 7 and 8.

In step 1, the cells 705 were loaded and cultured by introduction of a culture medium 700. Step 2 shows the provision of a layer of pre-coated RNA capture beads 1600 on top of the cells 705. A lysis mixture 700A is introduced in Step 3. This effects a break down of the cell walls and generates a lysate mixture 1605. The lysate mixture mixes with the beads and after about 30 minutes incubation the beads capture the cell RNA. In Step 4, the remains may be washed away by flowing through another volume of liquid such as PBS 1610.

Figure 17:
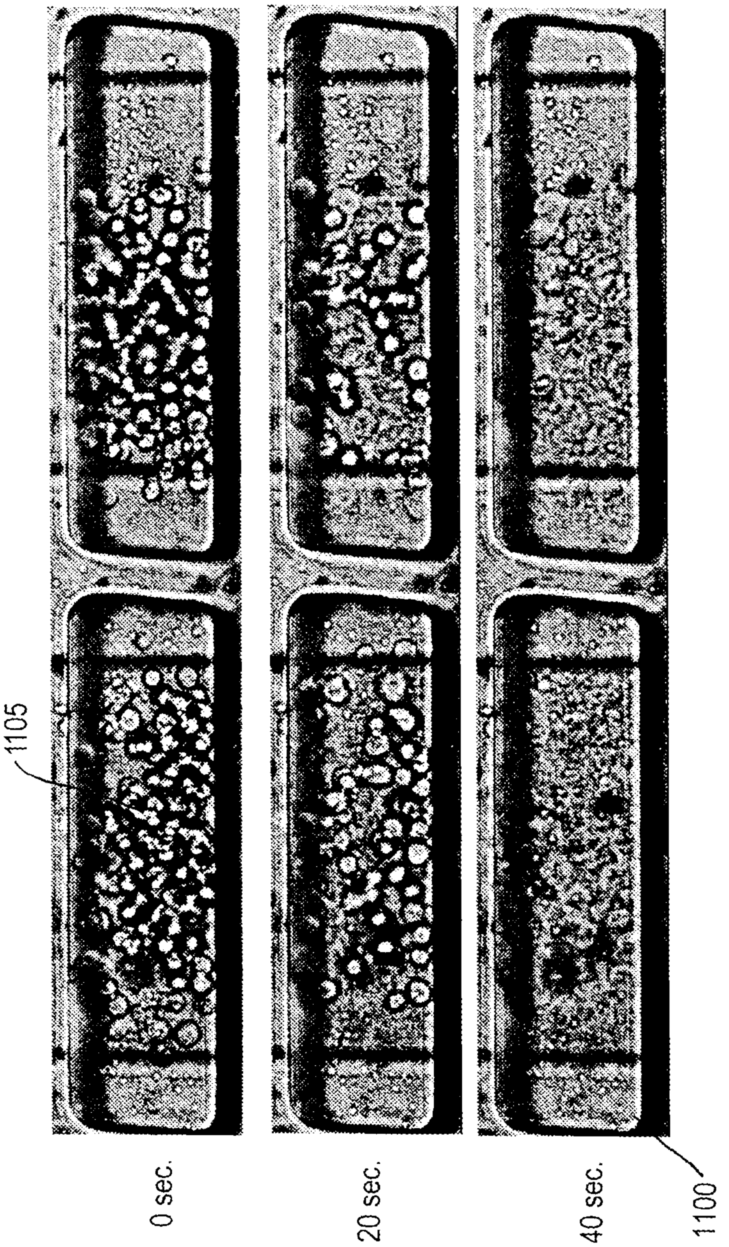
FIG. 17 shows exemplary data showing the effects of such cell lysis.

The results from a lysis experiment are shown in FIG. 17 where HeLA cells were lysed with a lysis agent in the form of 100 mM NaOH. The effective breakdown of the cell walls is complete within 40 seconds, as is evident from the disintegration of the cells shown with elapse of time.

Figure 18:
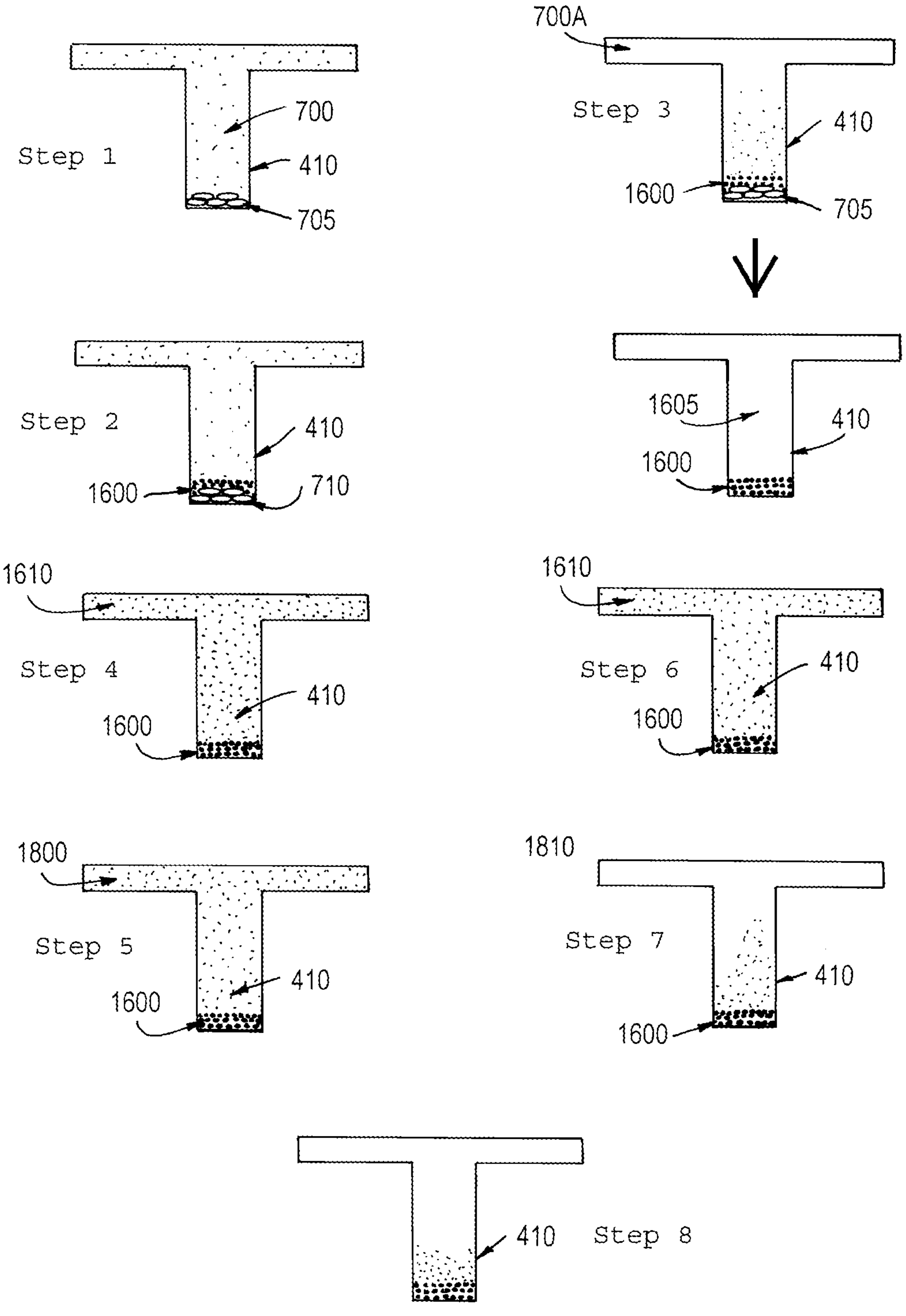
FIG. 18 shows exemplary steps that may be used in effecting NASBA.

A variety of tests may be conducted on cells that are constrained within the capture region. For example immunoassay and real time NASBA analysis can then be performed by following the steps shown in FIG. 18. During the real-time NASBA and immuno-assay analysis phase the device is mounted on a standard automated temperature controlled fluorescence microscope stage and the change in fluorescence from each capture region is measured as a function of time (FIGS. 19 & 20).

Figure 16:
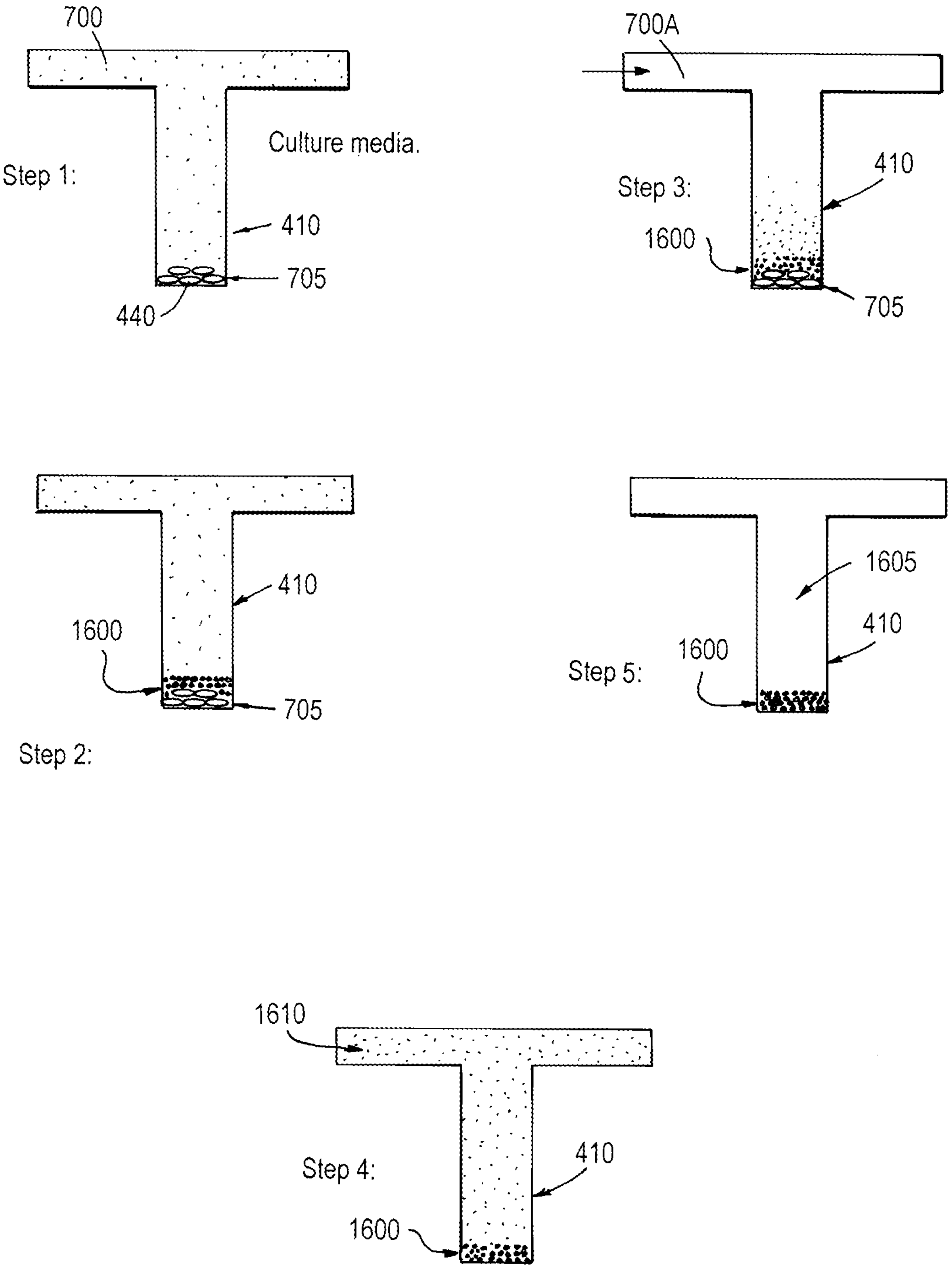
FIG. 16 shows how cell lysis may be effected.

Steps 1 through 4 are the same as what was described with reference to FIG. 16. In Step 5 a fluorescently labelled antibody mixture 1800 was introduced into the device. Unbound fluorescent anti-bodies may be washed away with PBS 1610 or other suitable washing or dilution materials, and the fluorescence measured. It will be appreciated that a complete washing may not be required in that the sequential flow of the additional fluid may simply effect a dilution of the previously entrained fluid within the chamber. —Step 6. Any fluorescence around an antibody coated bead is due to protein in the target. This fluorescence may be optically analysed. In Step 7 a NASBA reagent mixture 1810 was introduced into the device. Step 8 demonstrates how real time NASBA may be done by incubating the device at 41° C. and monitoring the increase in fluorescence in the capture region. Any increase in fluorescence can be attributed to generation of more amplicons and opening of molecular beacons. It will be appreciated that this sequence of steps shows how the same capture chamber 410 may be used as a receiving volume for a plurality of different fluids, each of the fluids having an effect on the cells or subsequent mixture resultant from the exposure of the cells to a previously introduced fluid.

Figure 19:
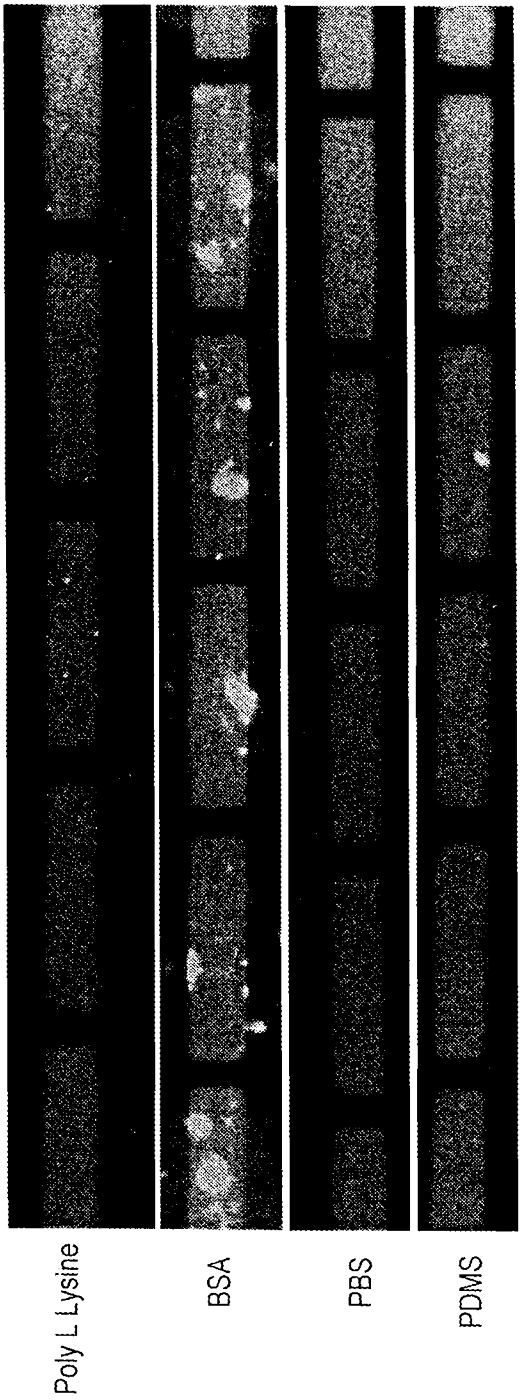
FIG. 19 shows fluorescence images of approx. 16 individual devices at the beginning of a NASBA reaction.
Figure 20:
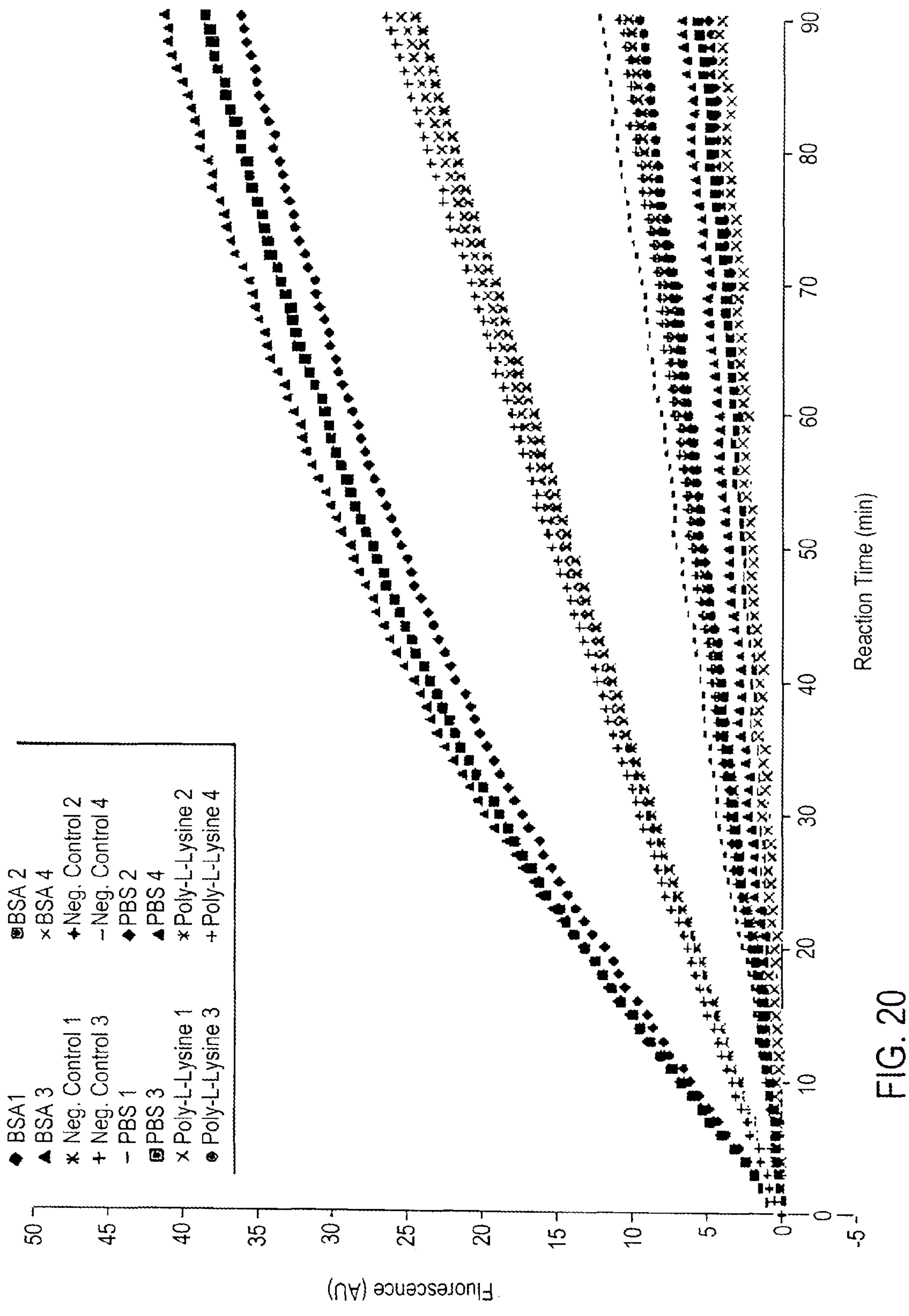
FIG. 20 shows simultaneous change in fluorescence within 16 devices during a NASBA reaction.

FIG. 19 shows fluorescence images of approximately sixteen individual devices at the beginning of the NASBA reaction. The different chamber coatings are also indicated. FIG. 20 shows simultaneous change in fluorescence within sixteen devices during the NASBA reactions. The coatings within the different capture regions was varied. Twelve positive control experiments were done, together with four negative controls within a single monolithic device.

It will be appreciated that the exemplary application of use of a device provided in accordance with the present teaching as a reaction chamber for NASBA type experiments demonstrates the useful employment of such a device for experiments that require contact between a captured cell and a sequence of fluids. By retaining the cell within a capture chamber or trench and then simply flowing different fluids past that captured cell, it is possible to achieve capture, labelling and analysis within a single structure. Therefore it will be understood that while the teaching has benefit and application in NASBA that it could also be used in other applications that require exposure of a captured cell to different fluids. Such application to lab on a chip technology with sample-in, experiment and answer out capability will be evident to those skilled in the art. Use of devices such as those heretofore described have benefit in that they can enable screening and diagnostics with lower cost, less contamination, and smaller sample volumes.

Figure 21:
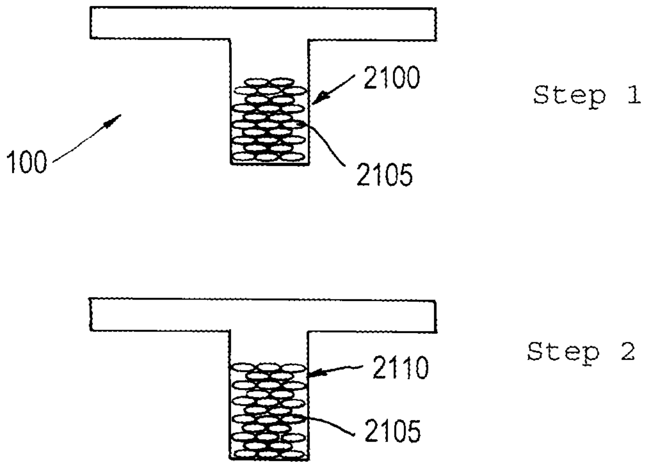
FIG. 21 shows examples of application of a device in accordance with the present teaching within a biomimetic environment.

The retention characteristics of the capture region make it particularly effective for also mimicking in vivo conditions of cellular activities. As the dimensions of the capture trench are much greater than the particles which are retained therein, devices such as those heretofore described can be usefully employed in biomimetic experiments. For example as shown in FIG. 21 a device 100 can be used to generate 3D cell structures 2100 of individual cancer cells 2105 so as to recreate cellular conditions similar to in-vivo tumours or other structures. This can also be combined with the fact that multiple cell types can be incorporated in a layered fashion to form co-cultures that further approximate in-vivo like conditions. An example of such a 3D co-culture like experimental setup for investigating cancer cell dynamics close to blood vessels 2110 (endothelial cells) is shown in Step 2 of FIG. 21. By selectively varying the nature of the fluid passing over the capture chamber it is possible to selectively layer the particles that are ultimately captured within the chamber. As these will typically be retained in the order that they were introduced into the chamber, this allows for subsequent experiments to be conducted within pseudo in vivo conditions. While the arrangements described herein preferentially retain the particles within the trench it is possible to modify the arrangement so as to provide for subsequent movement of the particles—either within the trench so as to provide for mixing or the like, or to effect removal of the particles out of the trench. Such arrangements will typically require a capacity to manipulate the particles and this can be conducted either before or subsequent to capture of the particles within the trench. Examples of techniques that could be employed include:

Acoustic
Magnetic
Inertial
Electric
Dielectrophoretic
Thermo-hydrodynamic
Laser tweezers
Hydrodynamically induced agitation
Specific or unspecific attachment to surface It will be understood that the use of such techniques may require an external source of agitation or manipulation of the particles.

A further example of the use of such a capture chamber is in the analysis of *E. Coli* bacterial cells. To provide for such analysis, a solution containing the *E. Coli* is flown into the device in a manner as described heretofore. This capture allows for cell based assays to be conducted. As part of the process for such analysis initially the device is loaded with the bacterial solution. After this initial loading, a washing or dilution solution is flown in to rinse out any non captured bacteria. Due to the low flow field at the bottom of the processing chamber trench, the bacteria present there will be effectively captured and not washed away. Due to the very low density of the *E. Coli* bacteria, the capture efficiency is much lower than that of denser particles or cells such as cancer cells.

Figure 22:
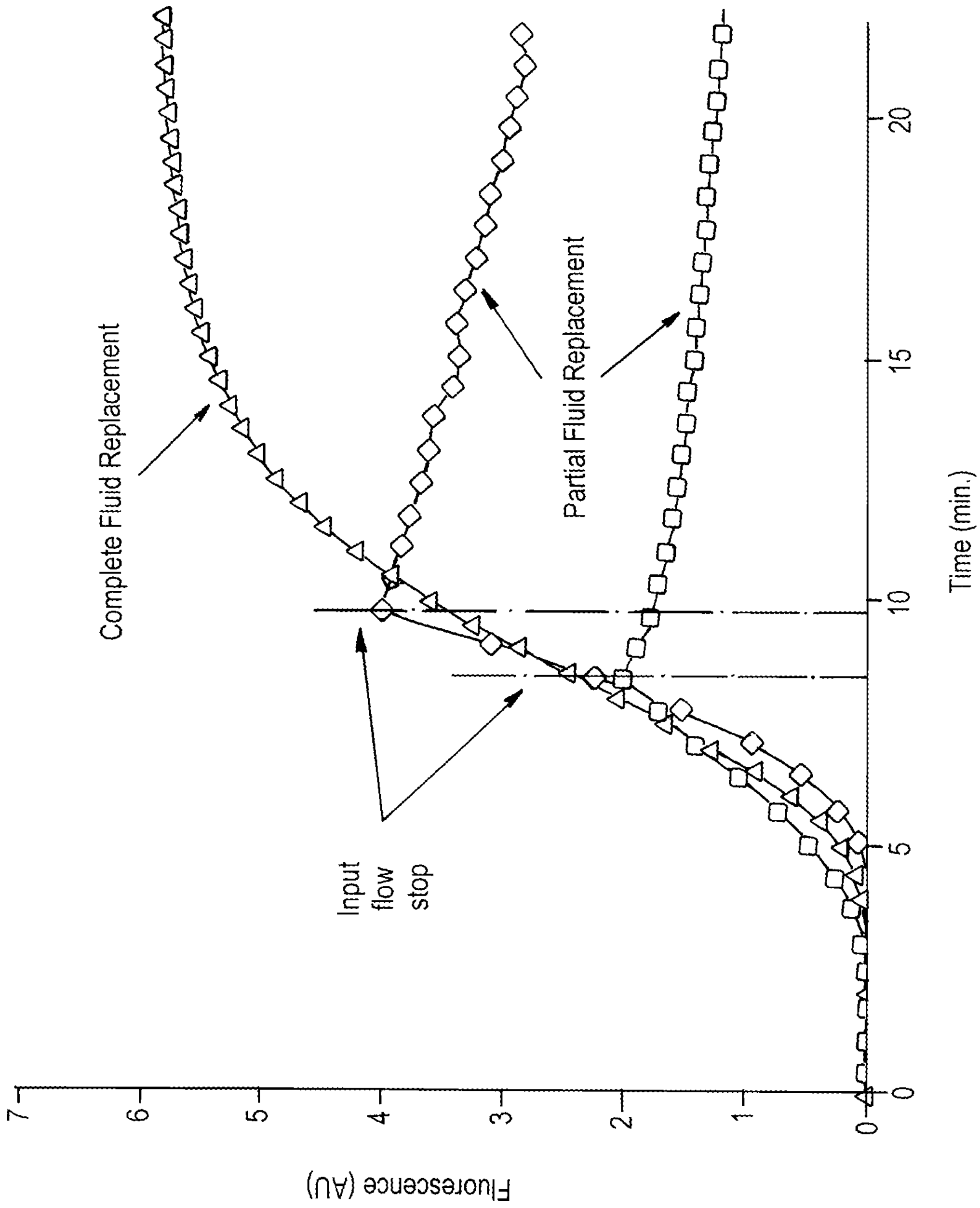
FIG. 22 shows how mixing may be effected within a device in accordance with the present teaching.

If mixing of fluids is required between a new input fluid and the previous contents of the processing chamber, then that may be achieved by stopping the input fluid flow before it has completely replaced the previous contents as shown in FIG. 22. In this specific example it is shown how a FITC dye (44 μM) is flown into a previously water filled device and allowed to mix with the water within the trench chamber. The input flow velocity is ~400 μm/sec In cases where reagent or sample volumes are very limited and scarce an oil layer may be used to hydrostatically drive in the low volume reagents. Experiments with 20 microliter tips demonstrated that volumes as low 400 nL can be readily loaded into the processing module. Since each module consists of 8 processing chambers each chamber is loaded with 50 mL. Due to the oils lower density, input flow rates can be up to 25% slower compared to water solution based hydrostatic flow.

With on-chip gravity driven flow control, an array structure such as described heretofore is flexible and can be easily integrated into existing infrastructure and workflows such as robotic pipetting systems, incubators, and fluorescent microscope systems.

It will be appreciated that the capture chamber may be considered as a sediment trap whereby the particles within the fluid, such as for cells or other living organisms, which are entrained within the fluid on passing the capture chamber are displaced out of the fluid and remain in the capture chamber for subsequent analysis or experimentation. As they simply fall out of the fluid they are exposed to minimum shear stress. These particles will consolidate on the bottom of the capture chamber to provide what may be considered a sediment on the chamber base. As more particles are retained within the capture chamber, the height of the sediment will increase.

The devices described herein have been illustrated with reference to a single flow path and a single trench provided within that flow path. It will be appreciated that modifications to the individual devices described could include an array of sequentially defined trenches within the flow path, each of the trenches differing from the others in their affinity for particles of different sizes so as to enable sorting of particles based on their sedimentation characteristics.

In the context of a primary force providing for the delivery and/or movement of the fluid/particles within the devices, it is also possible in combination with a primary force to employ a second force which acts on the particles or the fluid flow to either supplement or counteract the effects of the first force on the fluid or particles. This could be employed either locally within the devices to cause specific movement of the flow/particles within specific regions of the device or could be applied as a general force to affect the overall flow/movement characteristics. Examples of such a second force which can be used to reinforce or suppress particle sedimentation/retention into the trench and/or liquid flow patterns the particle is exposed include:

Magnetic force (static or dynamic)
Buoyancy of high- or low-density particles
Dielectrophoresis It will be understood that in order to operate efficiently that specific second forces may require use of materials/particles/fluids that exhibit a response to these forces. For example use of paramagnetic beads could be employed where it is desirable to apply a magnetic force to effect movement of the beads.

Heretofore the liquids described have been generally homogenous in nature. It is possible to provide liquid sequencing within the context of devices provided in accordance with the present invention. Such liquid sequencing could employ one or more immiscible liquids where for example a second liquid, e.g. oil phase, seals a previously provided aqueous phase residing in trench. Within the context of the present teaching it is also possible to provide a train of mutually immiscible phases to feed different reagents to trenches. As another example, one of the liquids in the sequence may be (another) particle suspension from which particles might differentially sediment into the trench(es).

Devices provided in accordance with the present invention desirably provide for changes in the flow rate of the fluid passing through the device in regions proximal to the trench, the change of flow rate effecting a collection of particles from that fluid. It will be understood that different fluids may have different flow rates when exerted to the same force. This could be used as a means to preferentially collect particles from a first fluid in a first trench and particles from a second fluid in a second trench. While it is not intended to limit the teaching of present invention to any one set of specific parameters simulation analysis has shown the variations in the flow velocity magnitudes in the processing chamber and trench. Cell capture is achieved due to the flow velocity magnitude in the trench being approximately 3 orders of magnitude lower the flow above it. As a result of these variances, the particles that enter the low flow velocity region are effectively captured.

The particles/fluid that are collected and retained in the trenches can be subjected to a number of different tests such as for example:

- Microscopy techniques including staining
- Surface sensitive excitation and detection such as SPR, TIRF
- Other excitation and/or detection techniques.

The fabrication of devices provided in accordance with the present teaching may be effected using one of a number of different processes. While it is not intended to limit the teaching to any one specific process exemplary techniques that could be employed include:

- Injection moulding
- Hot embossing
- Thermoforming
- Precision engineering
- Laser ablation
- Lamination
- Lithography
- Dry and wet etching
- other microfabrication schemes including sealing schemes as will be appreciated by those skilled in the art.

It will be appreciated that a device such as that fabricated in accordance with the present teaching has a number of advantages including its application to efficient cell capture with minimal clogging and exposure of the cells to shear stress. The device is suitable for in situ cell culturing and can also be considered for providing 3-D cell co-culturing. An exemplary application has been demonstrated in multi-flow analysis techniques which may be effected without removal of the captured cells from their capture chamber. Such devices may be provided in single element packages or could be arranged in array structures where a plurality of devices share a common input. Further modification has been described in the context of a multiplexed structure that provides multiple capture regions within the same substrate. These devices can be implemented or fabricated using conventional microfluidic engineering principles. Use of plurality of devices provides for fluidic isolation of separate modules on a single chip. While it is not intended to limit the teaching to any one specific arrangement, the introduction of a fluid into the devices using integrated gravity driven pumping units on a monolithic micro device is particularly useful.

Figure 23:
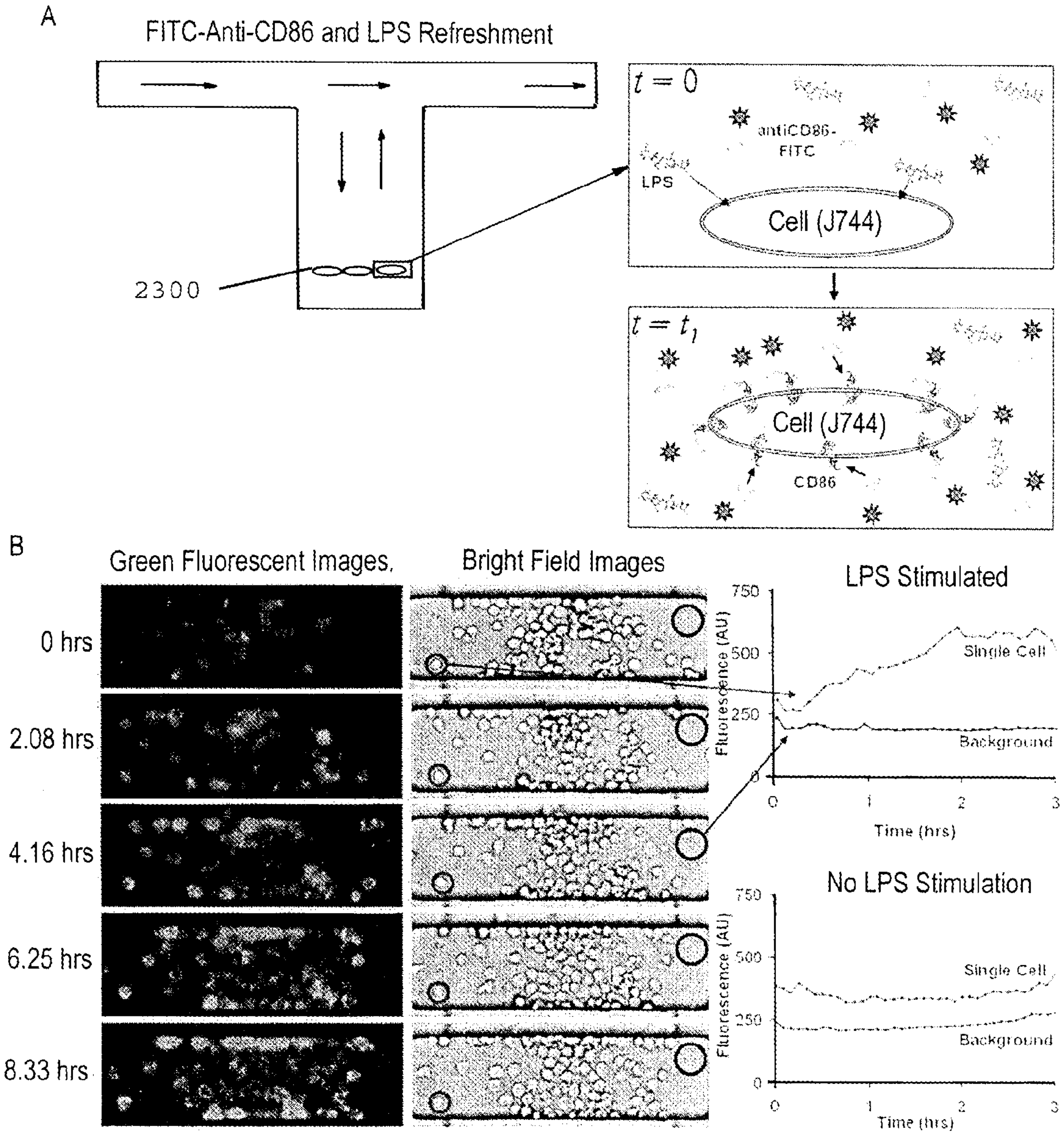
FIG. 23 shows how a device in accordance with the present teaching may be used for real time protein analysis.

A further example of use of such a multi-flow sequential analysis tool is in real-time protein analysis whereby it is possible to monitor live cell interactions with stimulation agents and/or other cells and in real time detect with high specificity the expression of surface proteins. FIG. 23 shows an example of such an application whereby the real time measurement of the level of surface protein expression may be effected. This exemplary procedure is based on the specific binding of labelled antibodies to the surface protein of interest (target proteins). The real-time measurement is achieved by having the surface protein within a microfluidic system that constantly refreshes a low concentration of antibodies in the medium. As new target proteins are expressed on the surface, the labelled antibodies in the medium solution specifically bind and label the proteins. The consumed anti-bodies are replaced by microfluidic refreshment so as to keep a constant supply of dissolved antibodies. The surface protein concentration is directly correlated to the signal from the surface labels.

It will be understood that this application advantageously employs the use of the microfluidic trench structure that has been described heretofore. Whereas in the previous applications described herein the structure has been demonstrated to be capable of very efficient cell capture and retention coupled with constant perfusion and refreshment of the soluble factors within the trench, in this application the present inventors have realised that the exact elements required for real time surface protein expression detection can be achieved with microfluidic systems. The capability of real time protein expression detection has not been previously demonstrated or reproduced in the macro-scale or with conventional equipment. The real time protein expression measurement was achieved by maintaining a very low concentration of fluorescently labelled antibodies in the perfusion medium.

In this exemplary experiment of the applicability of the apparatus for this application FITC-labelled anti-CD86 antibodies were used at concentration 1/100 of neat. The fluorescent antibody in this case was specific to the CD86 co-stimulatory molecule. During an antigen-dependent inflammatory response macrophage cells are activated and over express co-stimulatory molecules such as CD80, CD86 and CD40 on their surface which helps induce an effective T-cell response. This is one of the key mechanisms and outcomes of activated macrophages that makes them behave as antigen presenting cells (APCs) and activates the adaptive immune system. During the real time monitoring of surface protein expression J774 macrophages 2300 were activated with LPS (200 ng/ml) in the positive control case, while in the negative control no LPS was present in the culture medium. As the stimulated macrophages began to express the CD86 proteins on the cell surface, the fluorescent CD86 antibodies generated a fluorescent signal from the cell surface. As the free solution antibodies are being consumed and bound on the cell surface, new ones replace them through the continuous perfusion and diffusion. This maintains a constant supply of in solution antibodies and enables the real time monitoring of the CD86 protein expression on the surface of the macrophage cells. Furthermore the micro-scale dimensions of the device keep the background fluorescence generated by the in solution antibody to a minimum, lowering the LOD to physiologically relevant levels. This measurement technique can be further enhanced by simultaneously using several antibodies with different fluorophore labels to generate simultaneous real time multiple surface protein readout with single cell resolution.

It will be appreciated that this application of the sequential flow analysis tool is based on the capabilities of the described microfluidic system to refresh dissolved agents. By using a low concentration of in-solution labelled antibodies combined with the small micro-dimensions of microfluidic cavities, a low background signal can be maintained while always having antibodies available for labelling. This way any incubation and washing steps, usually required in conventional immunoassays become unnecessary, enabling the real time labelling and monitoring of surface proteins as they are generated.

Figure 24:
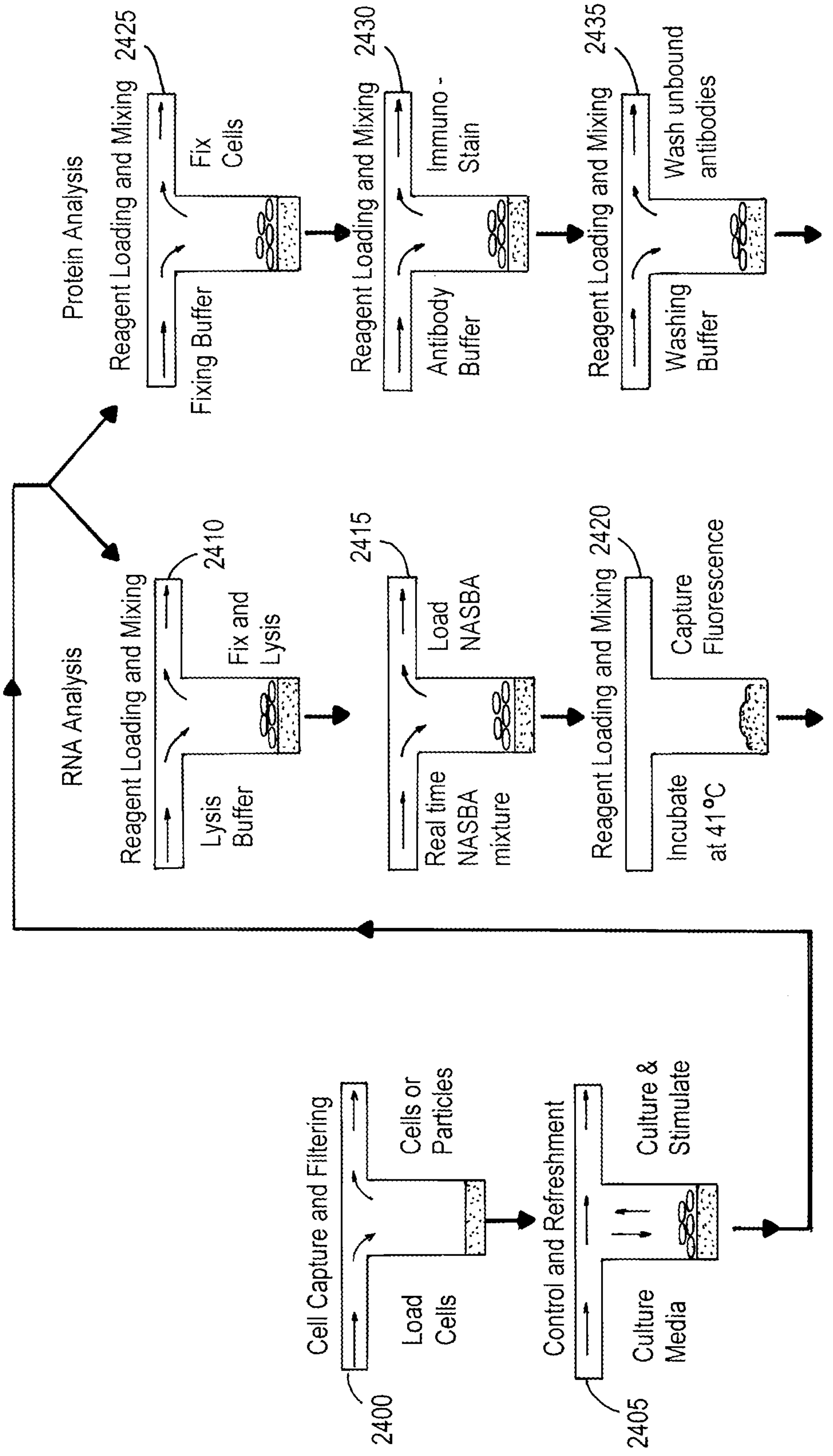
FIG. 24 shows a protocol that may be employed for gene and or protein expression analysis.

FIG. 24 shows in schematic form how the same device may be used for RNA analysis and protein analysis; the variation being on the reagents that are introduced into the individual chambers. While the figure schematically shows the two different analysis occurring in parallel, it will be understood that this is shown purely to emphasise the application of the sequential flow analysis apparatus of the present teaching to two different analysis.

In Step 2400, a common step, cells are loaded in a similar fashion to that which was described before. In Step 2405, these cells may be cultured and stimulated through introduction of a culture medium. The technique branches thereafter depending on whether RNA or protein analysis is desired.

In RNA analysis, firstly a fixing buffer followed by a lysis buffer are introduced to fix and lysis the cells (Step 2410). After a predetermined time period a real time NASBA mixture is introduced (Step 2415). After incubation at desired temperatures (about 41° C.) a fluorescence analysis (Step 2420) will provide the RNA analysis.

If protein analysis is preferred, then after the culturing of the cells (Step 2405), a fixing buffer is introduced to fix the cells within the chamber (Step 2425). Subsequent loading of an antibody buffer provides an immuno-stain (Step 2430). The subsequent washing of the unbound antibodies (Step 2435) and luminescent analysis of the chambers will provide information on the protein.

Figure 25:
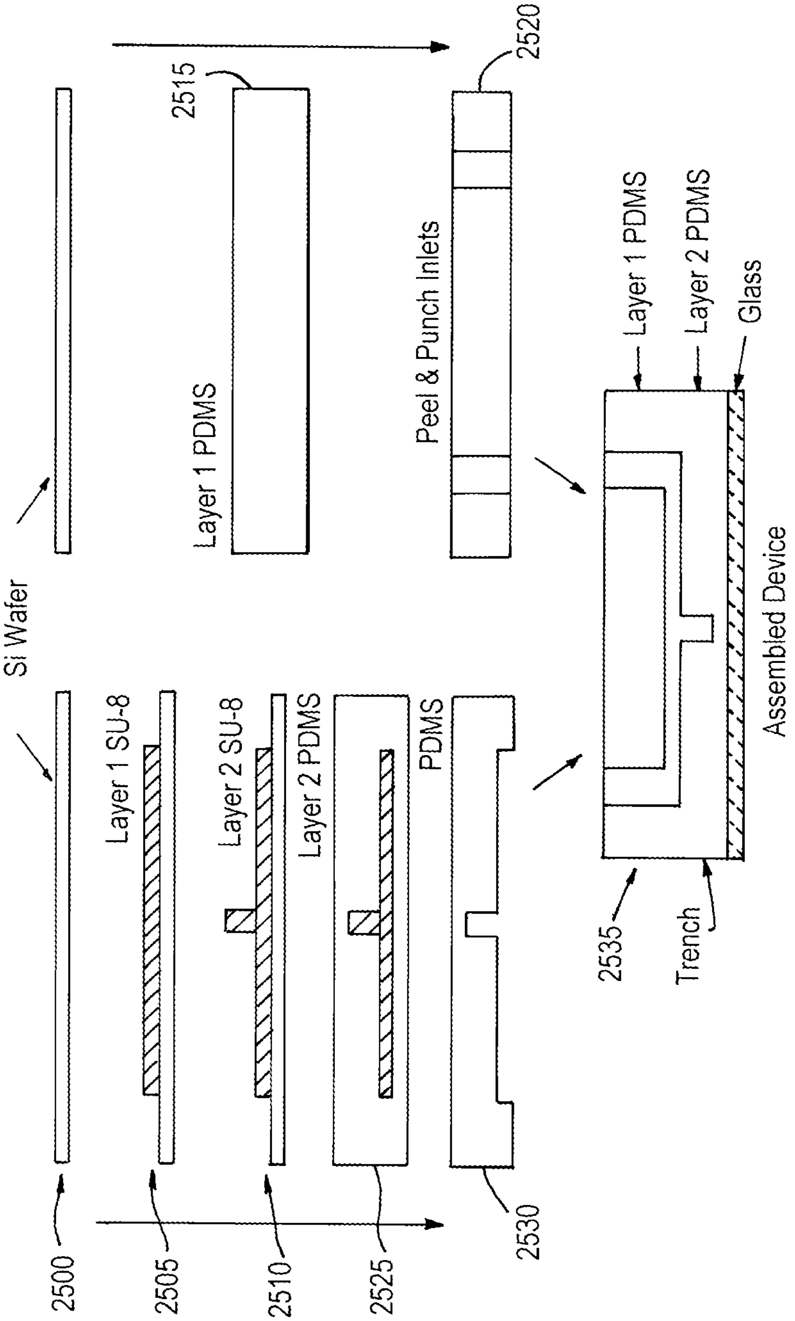
FIG. 25 shows in schematic flow exemplary steps that may be used to fabricate a device in accordance with the present teaching.

While a sequential multi-flow array may be fabricated in any one of a number of different methodologies, FIG. 25 shows an exemplary flow sequence that may be adopted to advantageously simplify the alignment and complexity of manufacture. In this exemplary arrangement two layers of PDMS (a fluidic layer and a lid/inlet layer) and a support glass substrate are employed. In Step 2500 two different Si wafers are provided. On a first wafer, a layer of SU-8 photoresist is provided (Step 2505). A second layer of SU-8 is then provided on the first layer to define an upstanding profile on the first layer (step 2510). On the second wafer a layer of PDMS is provided. This layer is then peeled and punched to generate what will ultimately form inlets to the device (Step 2520). On the first wafer a PDMS layer is provided over the SU-8 layer so as to encapsulate the layers (Step 2525). By suitable etching, the SU-8 may be eroded to define a pattern within the PDMS layer (Step 2530). By inverting this layer and then bringing the first and second layers together and assembling them relative to one another onto a glass substrate a trench and inlets are fabricated (Step 2535).

A technique such as that described herein can be used for analysis of cell secretion where cells secrete proteins into their surrounding extracellular fluid. By being able to spatially discriminate the detected optical signal it is possible to analyse the nature of the origin of the optical signal. To provide for spatial discrimination as to the origin of the desired optical signal it is necessary to be able to discriminate between the bulk contribution to the detected signal and that signal that originates from the sample or analyte of interest. One way of achieving this is to effect a mathematical integral technique whereby the detected intensity of the luminescent signal originating from the top of the collection chamber down to the surface of the sample region is compared with that originating from proximal or at the surface of the sample region. By ensuring adequate heights and dimensions of the collection chamber relative to the sample type and analysis technique effected it is possible to provide an adequate signal to noise ratio of sufficient level to allow for bulk and analyte contribution to the detected luminescence signal.

While the use of a luminescence based analysis methodology is particularly advantageous within the present context it will be understood that different optical agents could be used to allow for a spatial discrimination between the sample region and the bulk fluid within the collection chamber. For example different optical biosensing techniques could be used within the context of the present invention for assessing the properties of the captured cellular or particulate matter within the capture chambers or wells heretofore described.

It will therefore be appreciated that while the present teaching has been exemplified with reference to the heretofore and the attached drawings that these are provided to assist in an understanding of the teaching and are not to be construed as limiting in any fashion. Modifications can be made without departing from the spirit or scope of the invention. Where integers or components are described with reference to any one figure it will be understood that these could be changed for other integers or components without departing from the present teaching.

While a preferred arrangement of the present teaching will be evident from the claims that follow, the invention also relates to a microfluidic device substantially as described in the following numbered clauses.

1. A microfluidic device comprising a fluid path defined within a substrate between an input and an output, the device including a capture chamber provided within the fluid path, the capture chamber extending into the substrate in a direction substantially perpendicular to the fluid path such that operably particles provided within a fluid flowing within the fluid path will preferentially collect within the capture chamber due to action of a non-centrifugal force on the particles, the non-centrifugal force acting in a direction substantially parallel to the direction of extension of the capture chamber into the substrate.
2. The device of clause 1 wherein the fluid path is provided within the substrate, the fluid path defining a conduit having a base, top and side walls.
3. The device of clause 2 wherein the fluid path is disposed along an axis substantially parallel with an upper surface of the substrate.
4. The device of any preceding clause wherein the fluid path is proximal to an upper surface of the substrate.
5. The device of any preceding clause wherein the capture chamber is in the form of a trench having a mouth adjacent to and in fluid communication with the fluid path, the trench having sidewalls that extend substantially parallel to the direction of the of the capture force into the substrate from the mouth of the trench.
6. The device of clause 2 wherein the trench has a major axis that is substantially perpendicular to the fluid path, the trench being longer than it is wide.
7. The device of clause 6 dimensioned such that operably fluid travelling within the fluid path and entering downwardly into the trench will undergo deceleration and the fluid exiting the trench will undergo acceleration, the change of velocity within the trench causing particles within the fluid to be displaced from the fluid.
8. The device of any preceding clause wherein the particles are cells and the capture chamber is dimensioned such that cells entrained within the fluid will preferentially be displaced from the fluid and will remain in the capture chamber.
9. The device of clause 5 wherein the fluid path defines a taper region immediately upstream of the mouth of the trench, the taper region operably providing for a deceleration of fluid within the fluid path immediately preceding the mouth.

10. The device of clause 9 wherein the fluid path defines a funnel region immediately downstream of the mouth of the trench such that fluid exiting the trench will undergo acceleration.

11. The device of clause 9 wherein the fluid path includes a fluid feed line upstream of the taper region, and wherein the side walls of the fluid path flare away from another between the feed line and the mouth of the trench.

12. The device of clause 10 wherein the fluid path includes a fluid waste line downstream of funnel region, and wherein the side walls of the fluid path tapering towards one another between the mouth of the trench and the fluid waste line.

13. The device of clause 10 wherein the taper region has a length greater than the funnel region.

14. The device of any preceding clause wherein the inlet is dimensioned to receive a pipette funnel such that fluid may be introduced into the device and then pass within the fluid path.

15. The device of clause 14 wherein the volume of the fluid within the pipette is related to the fluid flow rate within the device.

16. The device of clause 14 or 15 wherein the fluid enters into the device under hydrostatic pressure.

17. The device of any one of clauses 1 to 14 being dimensioned such that a fluid loaded into the device enters or moves within the device under the influence of one or more of:

Hydrostatic pressure head (e.g. pipette tip or tilt)
Pressure-driven flow
Centrifugally propelled flow
Electrokinetic mechanisms 18. The device of any preceding clause wherein the fluid path defines a filter between the inlet and the capture chamber so as to effect a filtering of particulate matter of a predetermined dimension prior to the capture chamber.

19. The device of any preceding clause including a plurality of capture chambers sequentially provided within the fluid path.

20. The device of clause 19 wherein individual capture chambers are configured so as to be operably predisposed to capture of particles of a particular characteristic.

21. The device of any preceding clause wherein the capture chambers comprises surfaces having a surface coating which operably exhibits an affinity for predefined particles.

22. The device of any preceding clause wherein the capture chamber comprises a preloaded reagent.

23. A microfluidic array comprising a plurality of devices as detailed in any preceding clause.

24. The array of clause 23 wherein selected ones of the plurality of devices share a common input.

25. The array of clause 23 or 24 wherein selected ones of the plurality of devices share a common output.

26. The array of clause 25 wherein the input is arranged in a branch structure such that fluid introduced into the input will be directed towards each of the capture chambers of the selected ones of the plurality of devices.

27. The array of clause 26 wherein the output is arranged in a branch structure such that fluid exiting each of the capture chambers of the selected ones of the plurality of devices will collect with fluid of others of the selected ones of the plurality of devices.

28. A multiplexed microfluidic structure including a plurality of arrays as detailed in any one of clauses 23 to 28.

29. The structure of clause 28 wherein the plurality of arrays are arranged in rows on a common substrate.

30. The structure of clause 28 or 29 wherein the plurality of arrays are spaced apart from one another such that the plurality of arrays can be concurrently loaded with fluid.

31. A biomimetic analysis tool comprising a device as detailed in any one of clause 1 to 22.

32. The tool of clause 31 wherein the capture chamber is dimensioned to receive a plurality of cells which on receipt within the chamber are predisposed to adopt a 3-D configuration.

The words comprises/comprising when used in this specification are to specify the presence of stated features, integers, steps or components but does not preclude the presence or addition of one or more other features, integers, steps, components or groups thereof.

The invention claimed is:

1. A multi-sequential flow sedimentary sample apparatus comprising a microfluidic device, the device comprising:

a fluid path defined within a substrate between an input and an output, the device including a capture chamber provided within and extending transverse to and fully across the fluid path, the capture chamber configured within the device to selectively capture particles travelling within a fluid in the fluid path such that these particles must traverse the capture chamber and will be displaced into the capture chamber from the fluid in the fluid path and remain in the capture chamber as the fluid flows over the capture chamber, the capture chamber being dimensioned and extending into the substrate in a direction substantially perpendicular to the fluid path such that operably particles of a predefined dimension provided within a fluid flowing within the fluid path will preferentially collect within the capture chamber due to action of a gravitational force on the particles, the gravitational force acting in a direction substantially parallel to the direction of extension of the capture chamber into the substrate such that the particles will operably sediment in the capture chamber, and wherein the apparatus is configured for sequential fluid engagement with a plurality of fluid supply lines, an engagement of the apparatus with a fluid supply line and receipt of fluid from that supply line operably effecting a discharge from the capture chamber of a previously provided fluid.

2. The apparatus of claim 1 wherein the device fluid path provided within the substrate includes a conduit having a base, top and side walls.

3. The apparatus of claim 2 wherein the device fluid path is disposed along an axis substantially parallel with an upper surface of the substrate.

4. The apparatus of claim 1 wherein the device fluid path is proximal to an upper surface of the substrate.

5. The apparatus of claim 1 wherein the device capture chamber is in the form of a trench having a mouth adjacent to and in fluid communication with the fluid path, the trench having sidewalls that extend substantially parallel to the direction of the capture force into the substrate from the mouth of the trench.

6. The apparatus of claim 5 wherein the trench has a major axis that is substantially perpendicular to the fluid path, the trench having a length parallel to the major axis greater than a length of the trench that is perpendicular to the major axis.

7. The apparatus of claim 6 wherein the a number of dimensions of the device are such that operably, fluid travelling within the fluid path and entering downwardly into the trench will undergo deceleration and the fluid exiting the trench will undergo acceleration, the change of velocity within the trench causing particles within the fluid to be displaced from the fluid.

8. The apparatus of claim 1 wherein at least one of the fluid supply lines comprises a filter provided between the inlet and the capture chamber such that operably particles of a predetermined dimension provided within the fluid travelling within the fluid path are filtered prior to the capture chamber.

9. The apparatus of claim 1 wherein the capture chamber is dimensioned such that discharge of a previously provided fluid does not effect corresponding discharge of the particles collected within the capture chamber.

10. The apparatus of claim 8 wherein the capture chamber is dimensioned such that introduction of a second fluid into the device effects a mixing of that second fluid with a previously provided fluid within the capture chamber.

11. The apparatus of claim 1 wherein the apparatus forms at least part of a real-time protein analysis tool.

12. The apparatus of claim 1 wherein the apparatus comprises at least part of a nucleic acid sequence-based amplification (NASBA) tool.

13. A sequential flow analysis tool comprising:

a microfluidic device comprising a fluid path defined within a substrate between an input and an output, the device including a capture chamber provided within and extending transverse to and fully across the fluid path, the capture chamber configured within the device to selectively capture particles travelling within a fluid in the fluid path such that these particles must traverse the capture chamber and will be displaced into the capture chamber from the fluid in the fluid path and remain in the capture chamber as the fluid flows over the capture chamber, the capture chamber extending into the substrate in a direction substantially perpendicular to the fluid path such that operably particles provided within a fluid flowing within the fluid path will preferentially collect within the capture chamber due to action of a gravitational force on the particles, the gravitational force acting in a direction substantially parallel to the direction of extension of the capture chamber into the substrate such that the particles will operably sediment in the single capture chamber;

means for introducing a flow of a first fluid into the input of the device and past the capture chamber, the introduction of the first fluid into the device effecting capture of particles within the first fluid within the capture chamber;

means for introducing a flow of a second fluid into the input of the device and past the capture chamber subsequent to the introduction of the first fluid, the flow of the second fluid past the capture chamber effecting a diffusion of the second fluid into the capture chamber so as to expose the retained particles to the second fluid.

14. The tool of claim 13 wherein a solution is formed on exposure of the retained particles to the second fluid, the tool further comprising:

means for introducing a flow of a third fluid into the device, the introduction of the third fluid and flow of that fluid past the capture chamber effecting a diffusion of the third fluid into the capture chamber so as to expose the solution to the third fluid.

15. The tool of claim 14 wherein the second fluid comprises particles, diffusion of the second fluid into the capture chamber effecting a collection of the particles of the second fluid within the capture chamber.

16. The tool of claim 15 wherein the captured particles are cells.

17. The tool of claim 14 wherein the capture chamber is dimensioned such that on introduction of the second fluid, a layering of the particles from the first and second fluids is provided within the capture chamber.

18. The tool of claim 14 wherein on introduction of the second fluid the particles of the first fluid react with the particles of the second fluid.

19. The tool of claim 14 comprising means for effecting movement of the particles within the capture chamber.

20. The tool of claim 14 configured for nucleic acid amplification.

21. The tool of claim 14 wherein the orientation of the extension of the capture chamber into the substrate is such that operably an external force acting on the particles within the capture chamber acts in a direction substantially parallel to the direction of extension of the capture chamber into the substrate.

* * * * *